United States Patent
Ren et al.

(10) Patent No.: US 9,899,609 B2
(45) Date of Patent: Feb. 20, 2018

(54) ORGANIC ELECTROLUMINESCENT COMPOUND AND ORGANIC PHOTOELECTRIC APPARATUS THEREOF

(71) Applicants: Shanghai Tianma AM-OLED Co., Ltd, Shanghai (CN); Tianma Micro-electronics Co., Ltd., Shenzhen (CN)

(72) Inventors: Hongyang Ren, Shanghai (CN); Xiangcheng Wang, Shanghai (CN); Wei He, Shanghai (CN)

(73) Assignees: SHANGHAI TIANMA AM-OLED CO., LTD., Shanghai (CN); TIANMA MICRO-ELECTRONICS CO., LTD., Shenzhen (CN)

( * ) Notice: Subject to any disclaimer, the term of this patent is extended or adjusted under 35 U.S.C. 154(b) by 0 days.

(21) Appl. No.: 15/164,053

(22) Filed: May 25, 2016

(65) Prior Publication Data
US 2017/0186973 A1 Jun. 29, 2017

(30) Foreign Application Priority Data
Dec. 25, 2015 (CN) .......................... 2015 1 0995695

(51) Int. Cl.
| | |
|---|---|
| B32B 9/00 | (2006.01) |
| H01L 51/00 | (2006.01) |
| C09K 11/02 | (2006.01) |
| C07D 209/86 | (2006.01) |
| C09K 11/06 | (2006.01) |
| H01L 51/50 | (2006.01) |
| H01L 51/56 | (2006.01) |

(52) U.S. Cl.
CPC ........ H01L 51/0072 (2013.01); C07D 209/86 (2013.01); C09K 11/025 (2013.01); C09K 11/06 (2013.01); C09K 2211/1007 (2013.01); C09K 2211/1029 (2013.01); H01L 51/001 (2013.01); H01L 51/5012 (2013.01); H01L 51/56 (2013.01)

(58) Field of Classification Search
CPC ............... H01L 51/0072; H01L 51/001; H01L 51/5012; H01L 51/56; C07D 209/86; C09K 11/025; C09K 11/06; C09K 2211/1007; C09K 2211/1029
USPC .......................................................... 428/690
See application file for complete search history.

(56) References Cited

FOREIGN PATENT DOCUMENTS

| | | | |
|---|---|---|---|
| CN | 103922995 A | 7/2014 | |
| CN | 104011894 A | 8/2014 | |
| JP | 2011153276 A | 8/2011 | |
| JP | 2011256143 A | 12/2012 | |
| KR | 1020110088457 A | 8/2011 | |
| KR | 20150089263 A | * | 8/2015 |
| KR | 1020150089263 A | 8/2015 | |
| TW | 201506125 A | 2/2015 | |
| WO | 2012002221 A1 | 1/2012 | |
| WO | 2015175678 A1 | 11/2015 | |

OTHER PUBLICATIONS

Translation of KR 1020150089263, Aug. 5, 2015.*

(Continued)

*Primary Examiner* — Hui Chin
(74) *Attorney, Agent, or Firm* — Anova Law Group, PLLC

(57) ABSTRACT

The present disclosure provides a nitrogen-containing heterocyclic compound having a general formula (I) and an organic photoelectric apparatus thereof. The general formula (I) is:

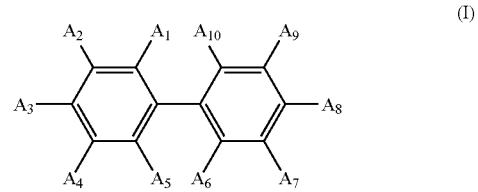

(I)

wherein $A_1$, $A_2$, $A_3$, $A_4$, $A_5$, $A_6$, $A_7$, $A_8$, $A_9$, and $A_{10}$ are independently selected from a hydrogen atom, a nitrile group and a function group having a general formula (II), and $A_1$, $A_2$, $A_3$, $A_4$, $A_5$, $A_6$, $A_7$, $A_8$, $A_9$, and $A_{10}$ include at least one nitrile group and at least one function group having the general formula (II), the general formula (II) being:

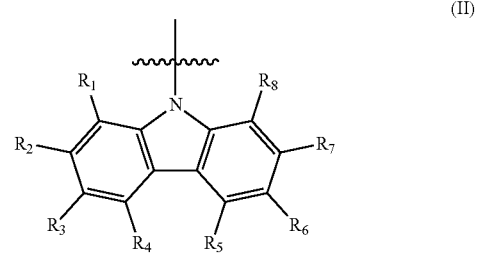

(II)

wherein $R_1$, $R_2$, $R_3$, $R_4$, $R_5$, $R_6$, $R_7$, and $R_8$ are independently selected from hydrogen atoms, deuterium atoms, $C_{6-30}$ aromatic group and $C_{2-30}$ heterocyclic aromatic group.

20 Claims, 3 Drawing Sheets

(56) References Cited

OTHER PUBLICATIONS

Cho et al., Angew. Chem., 127, 5290-5293, 2015.*
Cho et al., Adv. Mater., 26, 4050-4055, 2014.*
Yong Joo Cho, et al., A Universal Host Material for High External Quantum Efficiency Close to 25% and Long Lifetime in Green Fluorescent and Phosphorescent OLEDs, Advanced Materials, 2014, pp. 4050-4055.
Yong Joo Cho, et al., The Design of Dual Emitting Cores for Green Thermally Activated Delayed Fluorescent Materials, Angewandte Zuschriften, 2015, 5290-5293.

* cited by examiner

ORGANIC ELECTROLUMINESCENT COMPOUND AND ORGANIC PHOTOELECTRIC APPARATUS THEREOF

CROSS-REFERENCES TO RELATED APPLICATIONS

This application claims the priority of Chinese patent application No. 201510995695.6, filed on Dec. 25, 2015, the entirety of which is incorporated herein by reference.

BACKGROUND

Recently, organic light-emitting diode (OLED) has become a mostly focused new generation of display products because of its self-emitting characteristics, high-efficiency, wide color region, and wide viewing-angles, etc. The organic material used to form the OLED plays an important role in developing OLED.

When the organic material in a light-emitting layer of an OLED is electrically activated, the singlet excitons ($S_1$) and the triplet excitons ($T_1$) are generated. According to the self-spin statistics, the ratio of the singlet excitons ($S_1$) to the triplet excitons ($T_1$) is 1:3. According to the light-emitting principles, the materials of the light-emitting layer of the OLED include fluorescent materials and phosphorescent materials.

The fluorescent materials are only able to use 25% of singlet excitons (S1), which can be back to the ground state $S_0$ by a radiative transition. The phosphorescent materials are able to use not only the 25% of singlet excitons ($S_1$), but also 75% of the triplet excitons (T1). Thus, theoretically, the quantum efficiency of phosphorescent materials is 100%; and they are superior to the fluorescent materials when they are used in the OLED. However, the phosphorescent materials are usually rare metal complexes, the material cost is relatively high. Further, the blue phosphorescent materials have always been having issues on the efficiency and the lifespan when they are applied in the OLED.

In 2011, professor Adachi at Kyushu University, Japan, reported the thermally activated delayed fluorescence (TADF) material. Such a material presented a relatively good light-emitting performance. The band gap value of the $S_1$ state and the $T_1$ state of the TADF material is relatively small; and the lifespan of the $T_1$ excitons of the TADF material is relatively long. Under a certain temperature condition, the $T_1$ excitons may have a reverse intersystem crossing (RISC) to achieve the $T_1 \rightarrow S_1$ process; and achieve a radiative decay from the $S_1$ state to the ground state $S_0$. Thus, when the TADF material is used as the light-emitting layer in the OLED, the light-emitting efficiency of the OLED may be comparable to that of the OLED using the phosphorescence materials as the light-emitting layer. Further, the TADF material does not need rare metal elements. Thus, the material cost is relatively low.

However, the existing types of TADF materials are limited; and there is a need to develop more novel TADF materials with enhanced performance. The disclosed methods and material structures are directed to solve one or more problems set forth above and other problems in art.

BRIEF SUMMARY OF THE DISCLOSURE

One aspect of the present disclosure includes a nitrogen-containing heterocyclic compound having a general formula (I):

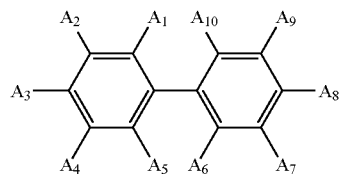

(I)

where $A_1$, $A_2$, $A_3$, $A_4$, $A_5$, $A_6$, $A_7$, $A_8$, $A_9$, and $A_{10}$ are independently selected from a hydrogen atom, a nitrile group and a function group having a general formula (II), and $A_1$, $A_2$, $A_3$, $A_4$, $A_5$, $A_6$, $A_7$, $A_8$, $A_9$, and $A_{10}$ include at least one nitrile group and at least one function group having the general formula (II), the general formula (II) being:

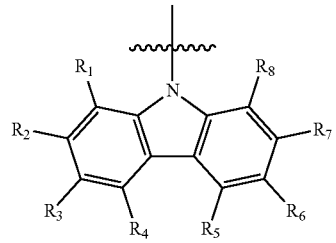

(II)

where $R_1$, $R_2$, $R_3$, $R_4$, $R_5$, $R_6$, $R_7$, and $R_8$ are independently selected from hydrogen atoms, deuterium atoms, $C_{6-30}$ aromatic group and $C_{2-30}$ heterocyclic aromatic group.

Another aspect of the present disclosure includes an organic photoelectric apparatus. The organic photoelectric apparatus includes an anode substrate, at least one organic layer formed over the anode substrate, and a cathode formed over the organic layer. The organic layer includes at least one nitrogen-containing heterocyclic compound having a general formula (I),

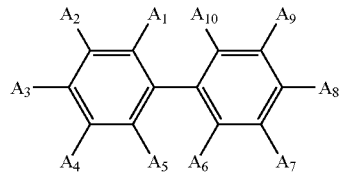

(I)

where $A_1$, $A_2$, $A_3$, $A_4$, $A_5$, $A_6$, $A_7$, $A_8$, $A_9$, and $A_{10}$ are independently selected from a hydrogen atom, a nitrile group and a function group having a general formula (II), and $A_1$, $A_2$, $A_3$, $A_4$, $A_5$, $A_6$, $A_7$, $A_8$, $A_9$, and $A_{10}$ include at least one nitrile group and at least one function group having the general formula (II), the general formula (II) being:

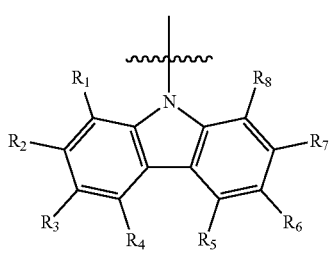

(II)

where $R_1$, $R_2$, $R_3$, $R_4$, $R_5$, $R_6$, $R_7$, and $R_8$ are independently selected from hydrogen atoms, deuterium atoms, $C_{6-30}$ aromatic group and $C_{2-30}$ heterocyclic aromatic group.

Another aspect of the present disclosure includes a process for fabricating an organic photoelectric apparatus. The method includes providing an anode substrate; forming at least one organic layer over the anode substrate; and forming a cathode layer over the organic layer, where the at least one organic layer includes at least one nitrogen-containing heterocyclic compound having general formula (I):

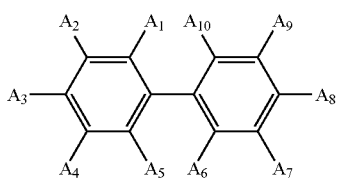

(I)

where $A_1$, $A_2$, $A_3$, $A_4$, $A_5$, $A_6$, $A_7$, $A_8$, $A_9$, and $A_{10}$ are independently selected from a hydrogen atom, a nitrile group and a function group having a general formula (II), and $A_1$, $A_2$, $A_3$, $A_4$, $A_5$, $A_6$, $A_7$, $A_8$, $A_9$, and $A_{10}$ include at least one nitrile group and at least one function group having the general formula (II), the general formula (II) being:

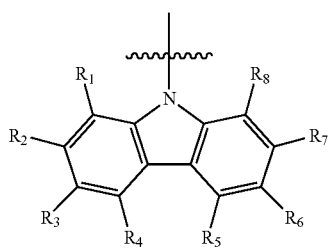

(II)

where $R_1$, $R_2$, $R_3$, $R_4$, $R_5$, $R_6$, $R_7$, and $R_8$ are independently selected from hydrogen atoms, deuterium atoms, $C_{6-30}$ aromatic group and $C_{2-30}$ heterocyclic aromatic group.

Other aspects of the present disclosure can be understood by those skilled in the art in light of the description, the claims, and the drawings of the present disclosure.

DETAILED DESCRIPTION

Figure 1:
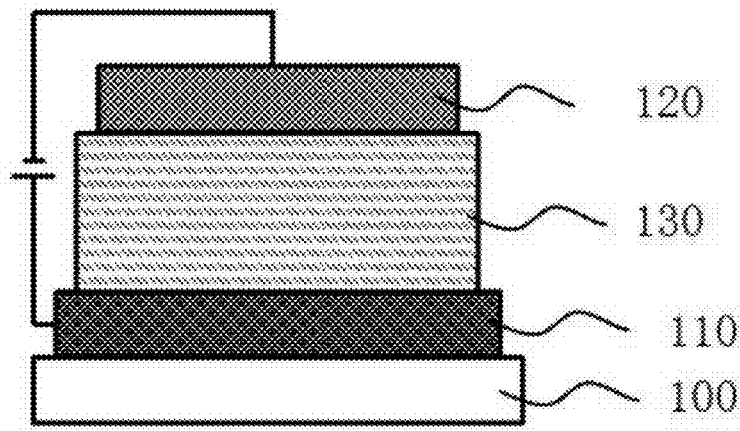
FIG. 1 illustrates an exemplary OLED consistent with the disclosed embodiments.

Reference will now be made in detail to exemplary embodiments of the invention, which are illustrated in the accompanying drawings. Wherever possible, the same reference numbers will be used throughout the drawings to refer to the same or like parts.

According to the disclosed embodiments, a compound of general formula (I) is provided. The general formula (I) may be:

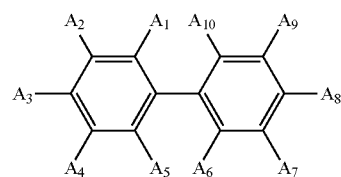

(I)

where $A_1$, $A_2$, $A_3$, $A_4$, $A_5$, $A_6$, $A_7$, $A_8$, $A_9$, and $A_{10}$ may be independently selected from a hydrogen atom, a nitrile group and a function group having a general formula (II), and $A_1$, $A_2$, $A_3$, $A_4$, $A_5$, $A_6$, $A_7$, $A_8$, $A_9$, and $A_{10}$ include at least one nitrile group and at least one function group having the general formula (II). According to the structure of nitrile group and the general formula (II), the disclosed compound may be referred to as a nitrogen-containing heterocyclic compound.

The general formula may be:

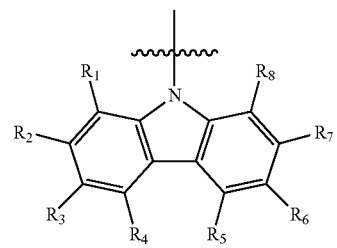

(II)

wherein $R_1$, $R_2$, $R_3$, $R_4$, $R_5$, $R_6$, $R_7$, and $R_8$ may be independently selected from hydrogen atoms, deuterium atoms, $C_{6-30}$ aromatic group, and $C_{2-30}$ heterocyclic aromatic group, etc.

In one embodiment, in the compound having the general formula (I), $A_1$, $A_2$, $A_3$, $A_4$, and $A_5$ may include at least one nitrile group and at least one function group having the generation formula (II). Further, $A_6$, $A_7$, $A_8$, $A_9$, and $A_{10}$ may include at least one nitrile group and at least one function group having the generation formula (II).

In certain other embodiments, in the compound having the general formula of (I), $A_1$, $A_2$, $A_3$, $A_4$, and $A_5$ may include at least one nitrile group without having a function group having the generation formula (II). Further, $A_6$, $A_7$, $A_8$, $A_9$, and $A_{10}$ may include at least one function group having the generation formula (II) without having the nitrile group. Further, the quantity of the nitrile group in $A_1$, $A_2$, $A_3$, $A_4$, and $A_5$ may not be greater than the quantity of the function group having the general formula (II) in $A_6$, $A_7$, $A_8$, $A_9$, and $A_{10}$.

In one embodiment, the energy level difference ($\Delta E_{st}$) between the lowest singlet state $S_1(E_{s1})$ and the lower triplet state $T_1(E_{T1})$ of the nitrogen-containing heterocyclic compound may be $\Delta E_{st} = E_{s1} - E_{T1} \leq 0.30$ eV, such as 0.29 eV, 0.28 eV, 0.27 eV, 0.26 eV, 0.25 eV, 0.24 eV, 0.23 eV, 0.22 eV, 0.21 eV, 0.20 eV, 0.19 eV, 0.18 eV, 0.17 eV, 0.16 eV, 0.15 eV, 0.14 eV, 0.13 eV, 0.12 eV, 0.11 eV, 0.10 eV, 0.09 eV, 0.08 eV, 0.07 eV, 0.06 eV, 0.05 eV, 0.04 eV, 0.03 eV, 0.02 eV or 0.01 eV, etc. If $\Delta E_{st} \geq 0.30$ eV, the fluorescence delay effect of the compound may not be obvious.

In one embodiment, the $\Delta E_{st}$ of the compound having the general formula (I) is smaller than approximately 0.25 eV. That is, $\Delta E_{st} \leq 0.25$ eV.

In certain other embodiments, the $\Delta E_{st}$ of the compound having the general formula (I) is smaller than approximately 0.15 eV. That is, $\Delta E_{st} \leq 0.15$ eV.

In still certain other embodiments, the $\Delta E_{st}$ of the compound having the general formula (I) is smaller than approximately 0.10 eV. That is, $\Delta E_{st} \leq 0.10$ eV.

In still certain other embodiments, the $\Delta E_{st}$ of the compound having the general formula (I) is smaller than approximately 0.05 eV. That is, $\Delta E_{st} \leq 0.05$ eV.

In still certain other embodiments, the $\Delta E_{st}$ of the compound having the general formula (I) is smaller than approximately 0.02 eV. That is, $\Delta E_{st} \leq 0.02$ eV.

In still certain other embodiments, the $\Delta E_{st}$ of the compound having the general formula (I) is smaller than approximately 0.01 eV. That is, $\Delta E_{st} \leq 0.01$ eV.

Such ranges of $\Delta E_{st}$ of the compound may have obvious fluorescent effect during a static tests.

In one embodiment, $R_5$, $R_6$, $R_7$, $R_8$, $R_9$, and $R_{10}$ may all be hydrogen.

In one embodiment, the present disclosed nitrogen-containing heterocyclic compound may be one selected from the following compounds 1-79.

1

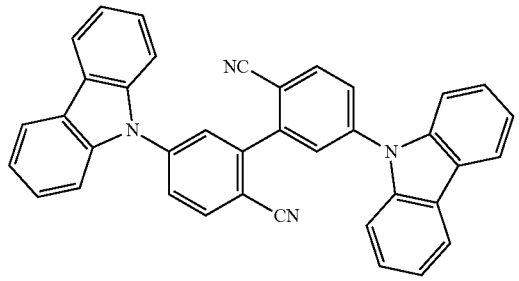

2

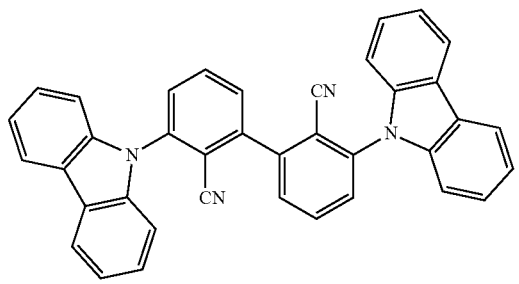

3

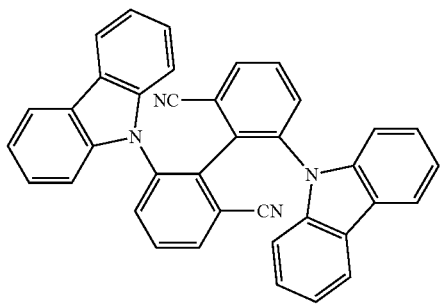

4

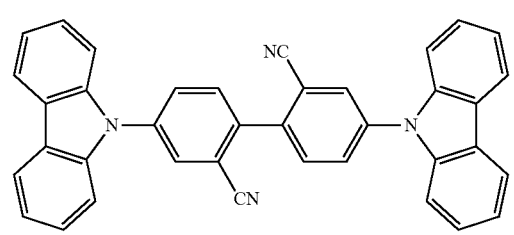

5

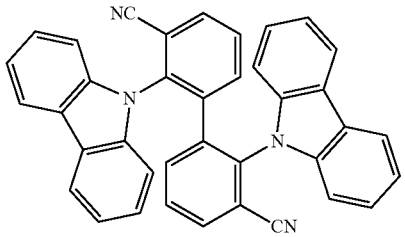

6

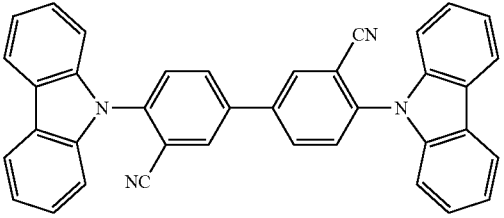

7

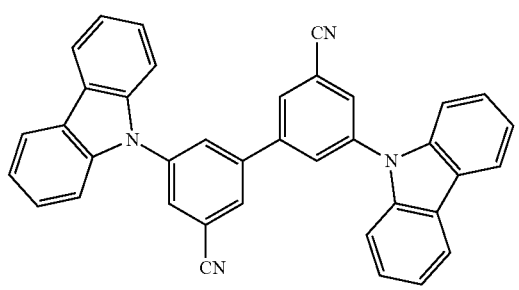

8
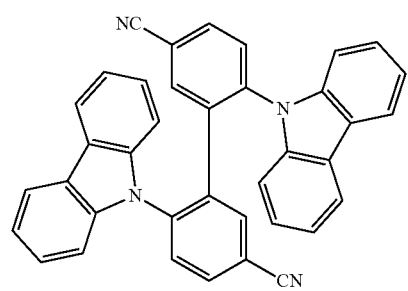
9
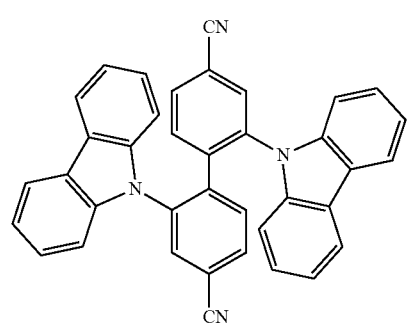
10
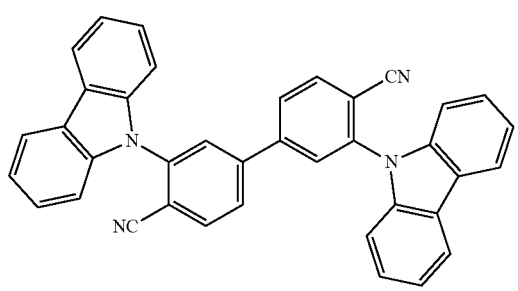
11
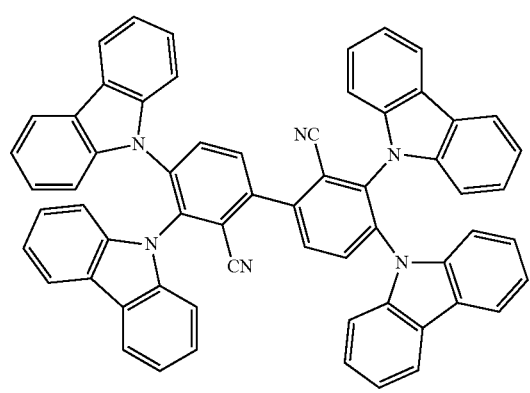
12
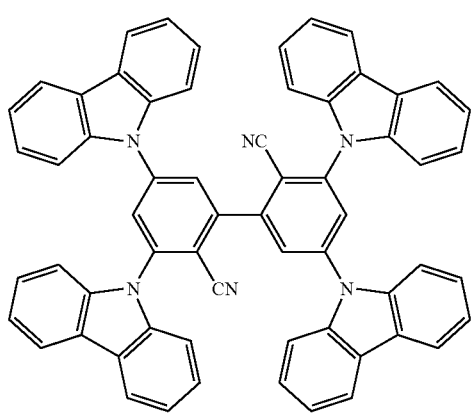
13
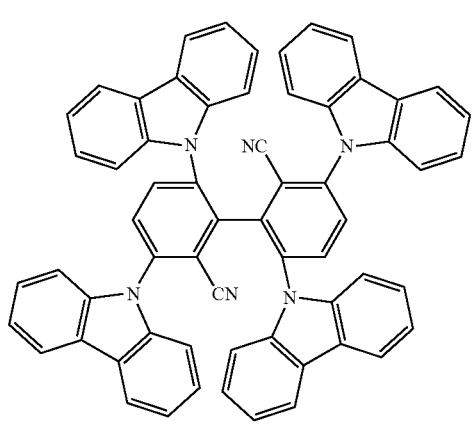
14
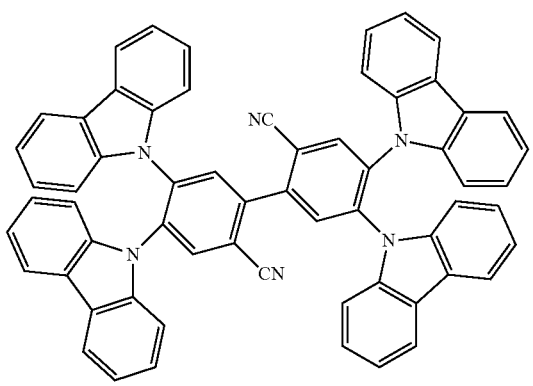

15
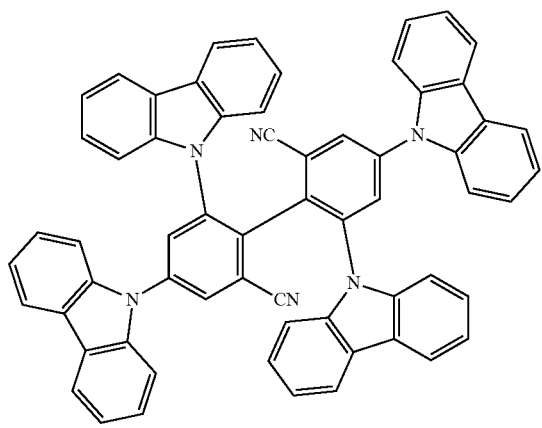
19
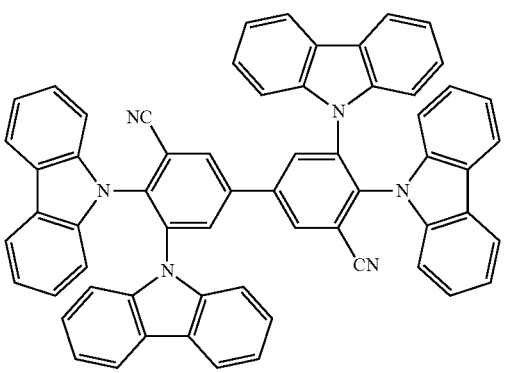
16
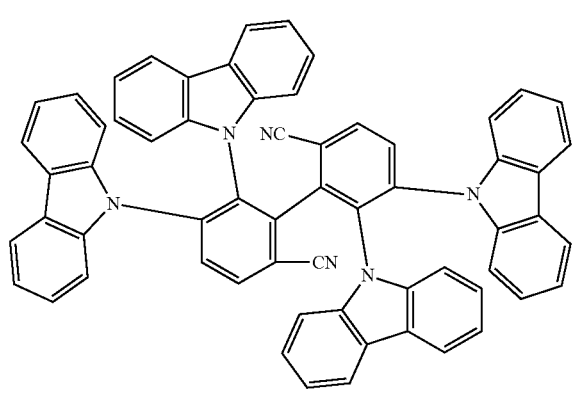
20
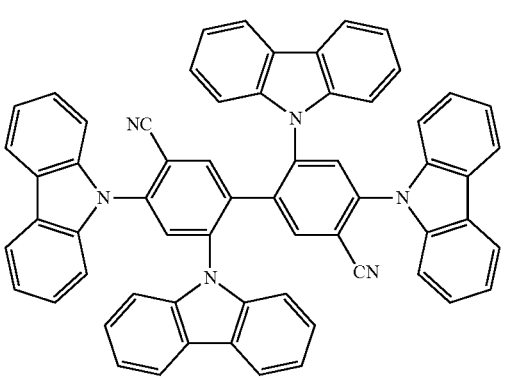
17
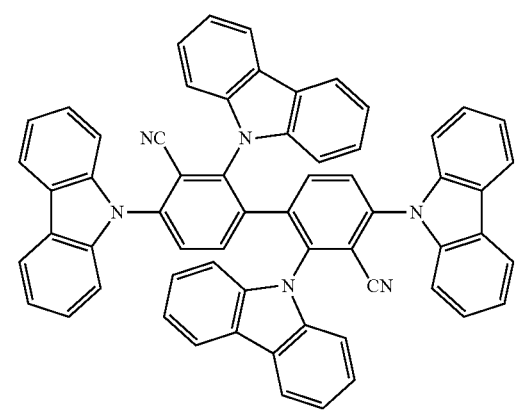
21
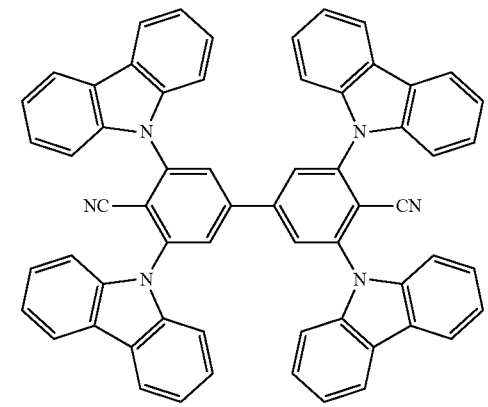
18
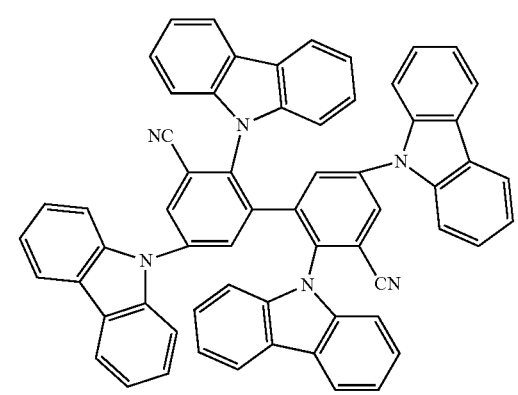
22
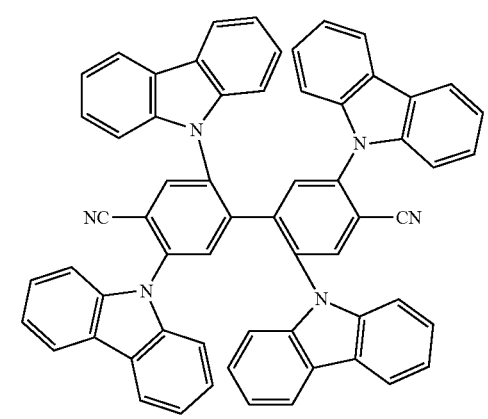

23
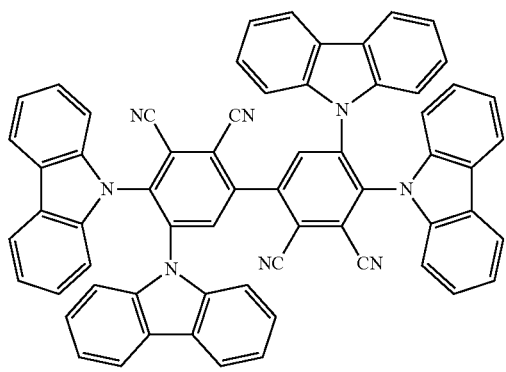
24
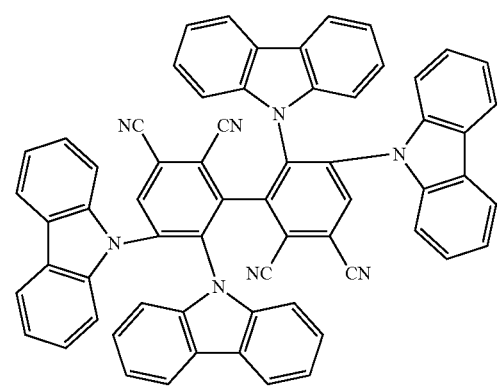
25
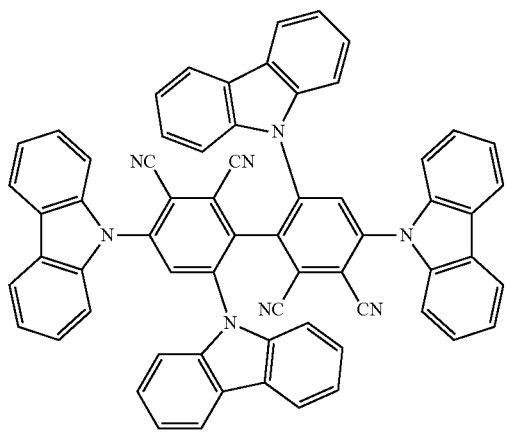
26
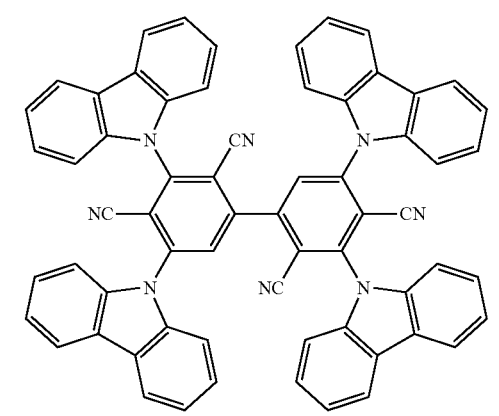
27
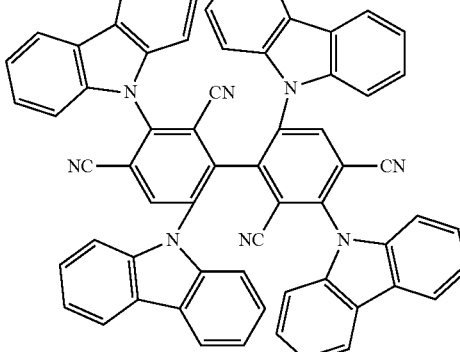
28
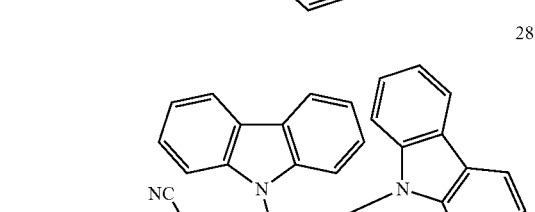
29
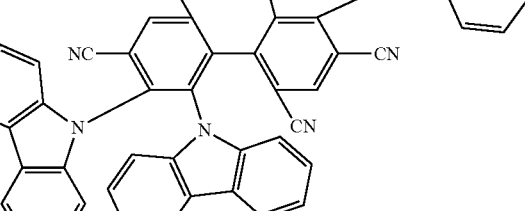
30
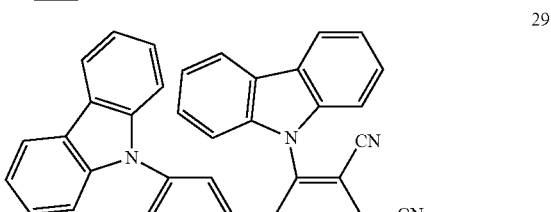

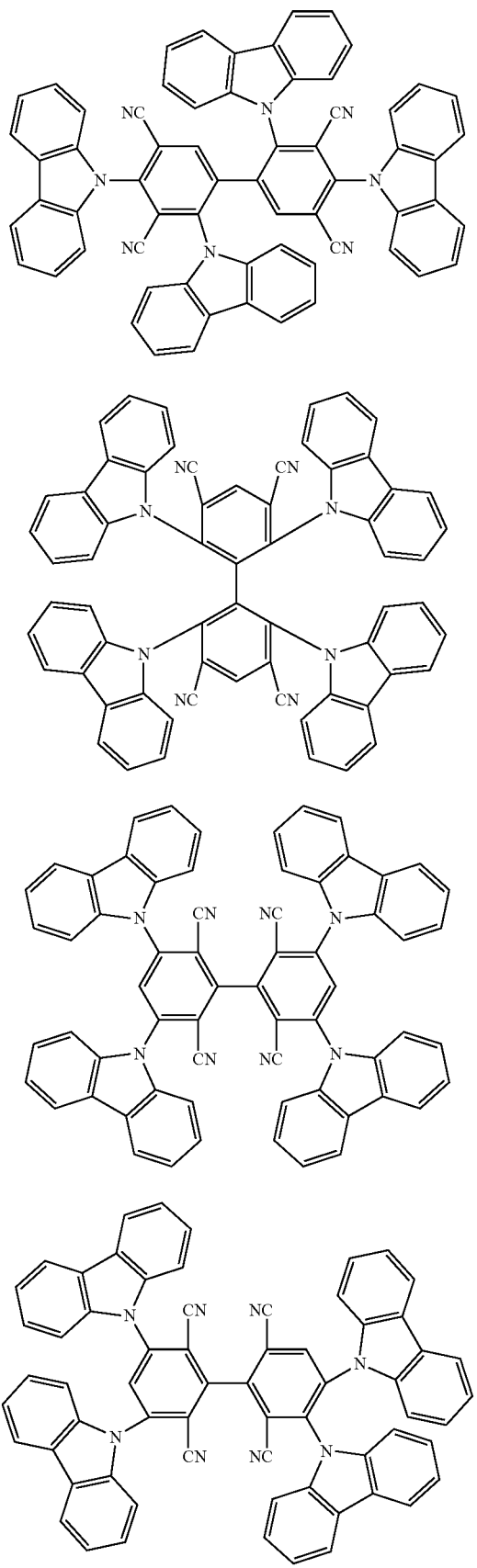
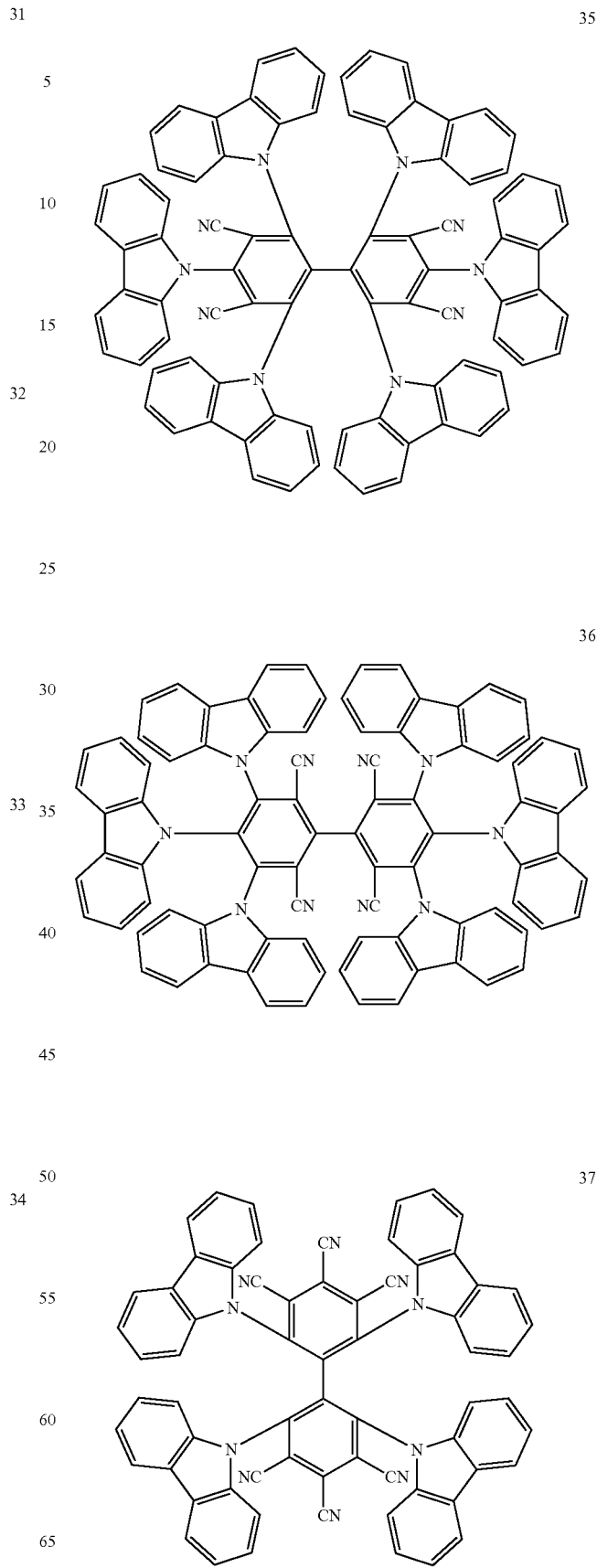

38
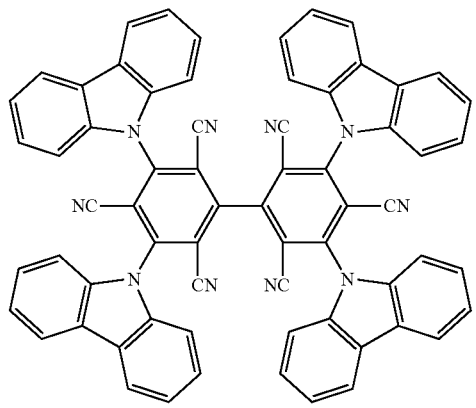
39
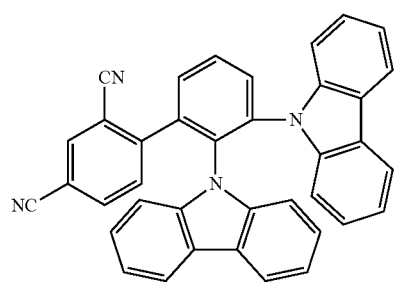
40
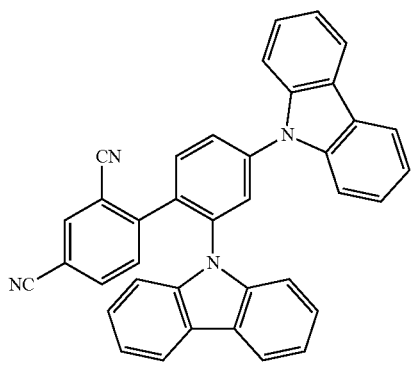
41
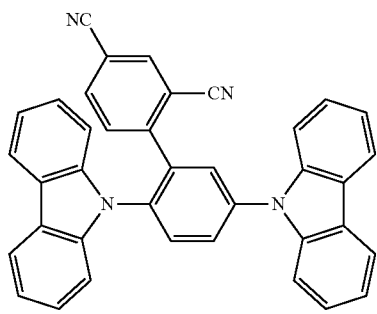
42
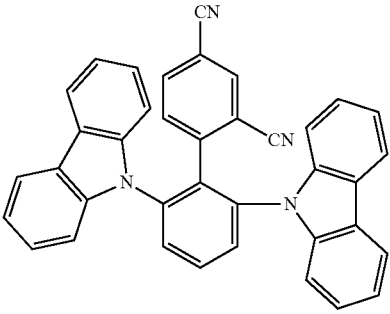
43
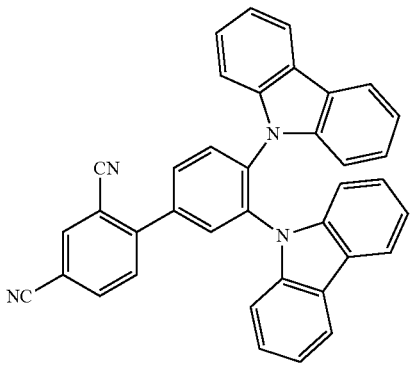
44
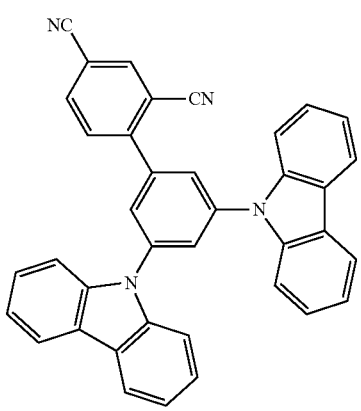
45
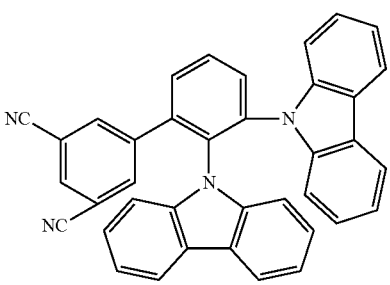

46
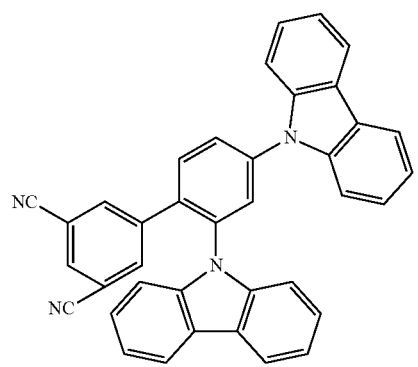
47
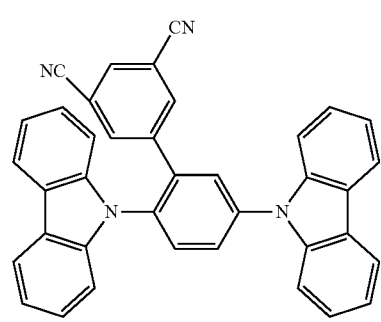
48
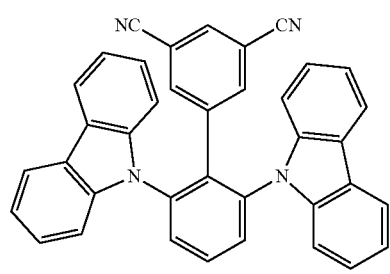
49
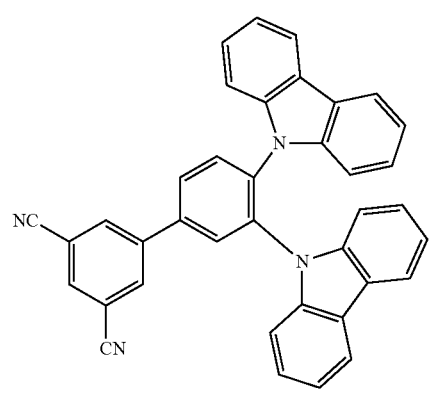
50
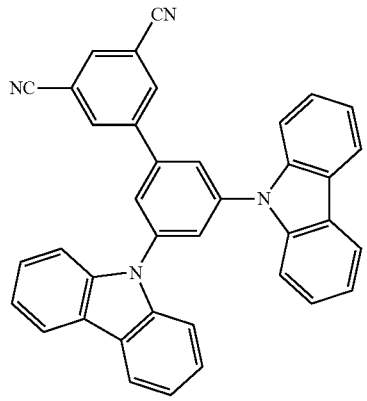
51
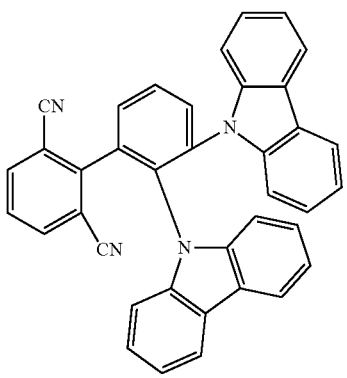
52
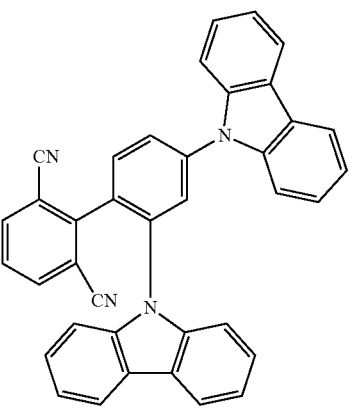
53
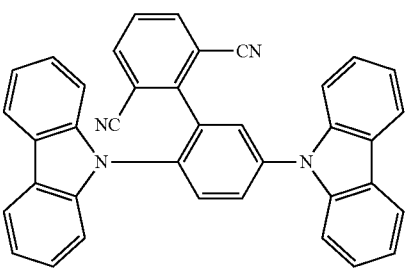

54
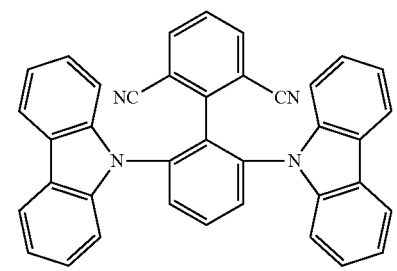
55
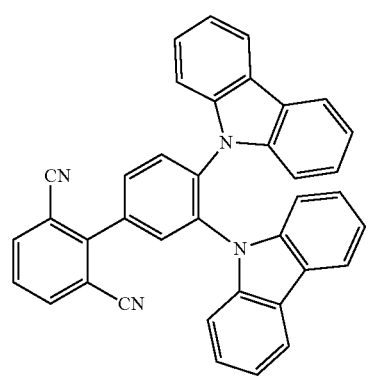
56
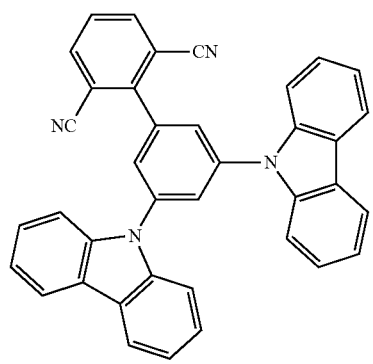
57
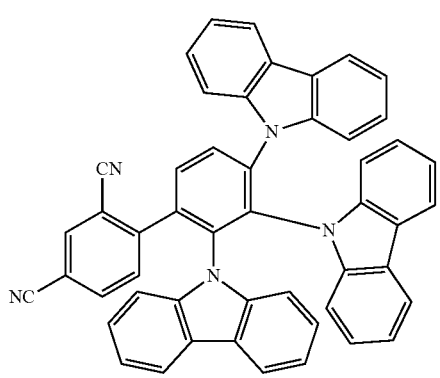
58
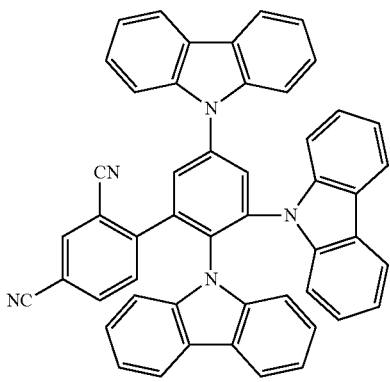
59
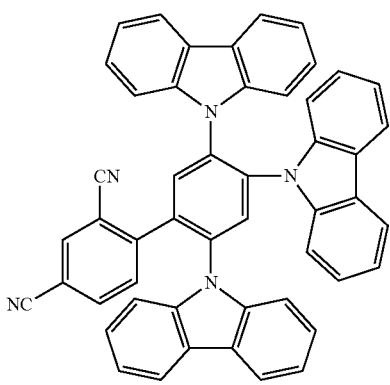
60
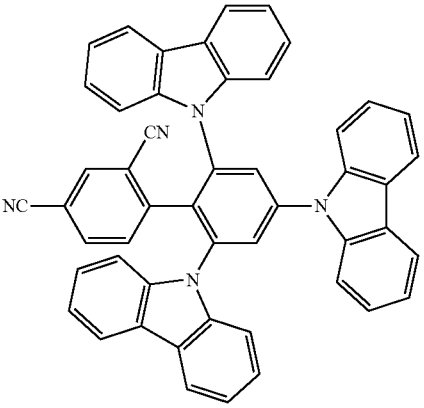
61
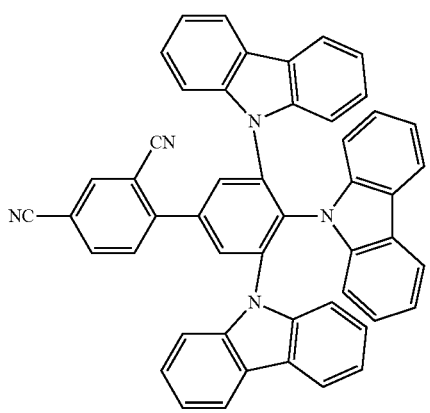

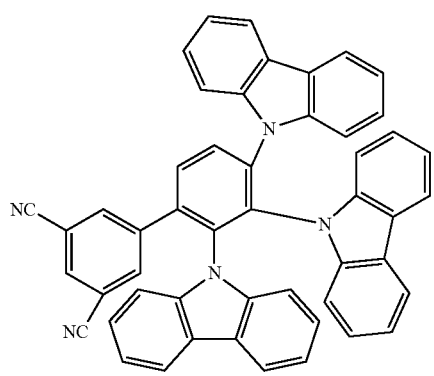
62
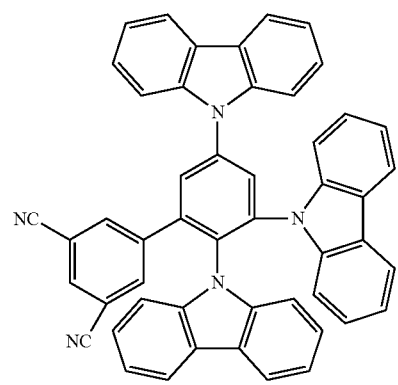
63
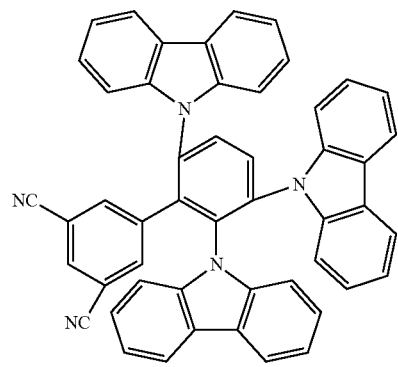
64
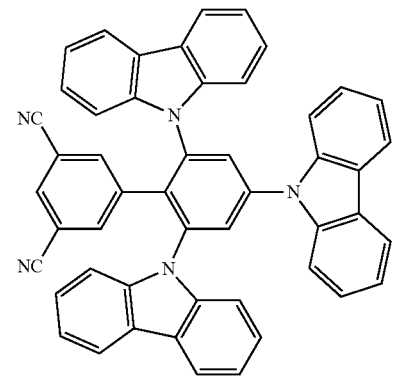
65
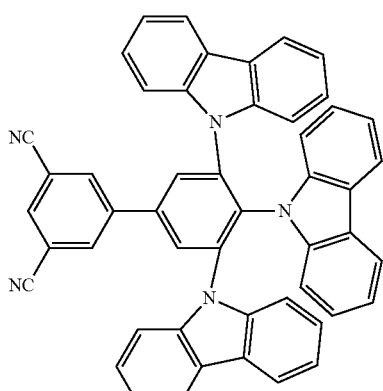
66
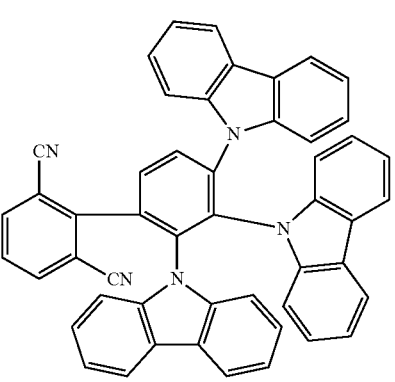
67
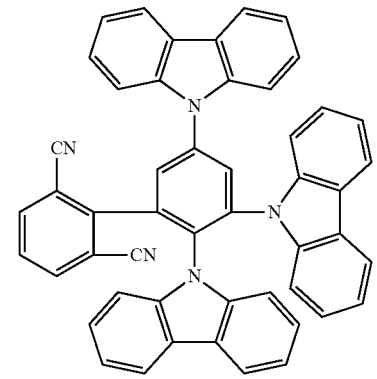
68
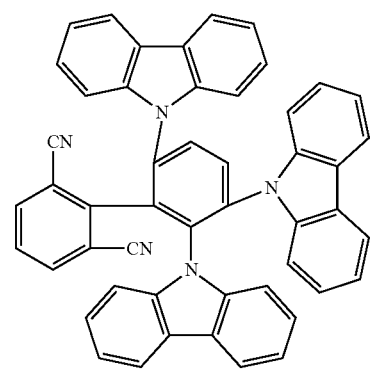
69

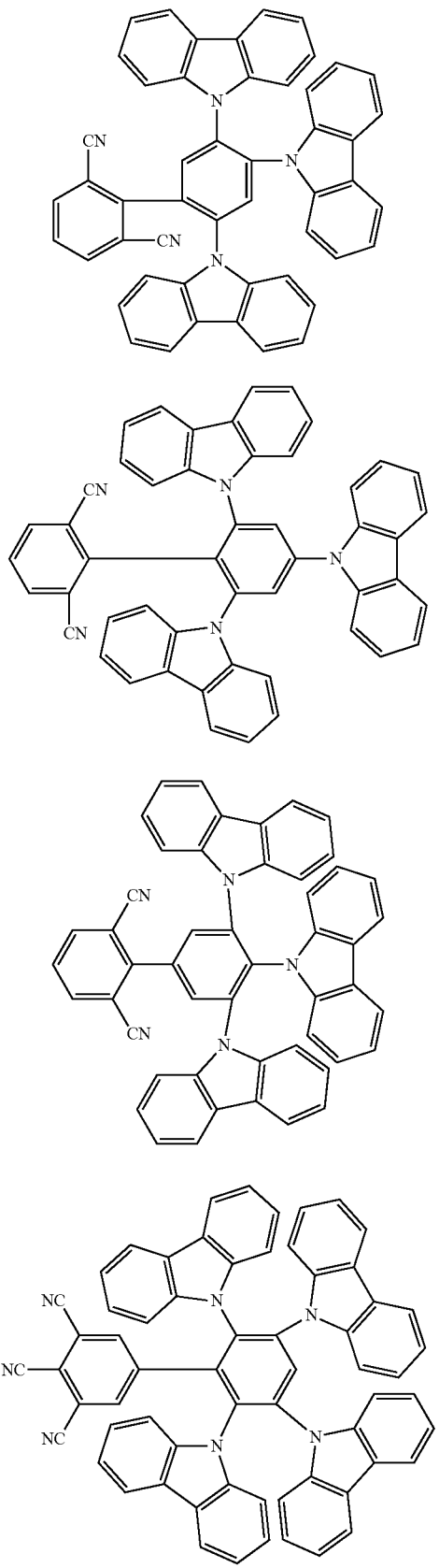
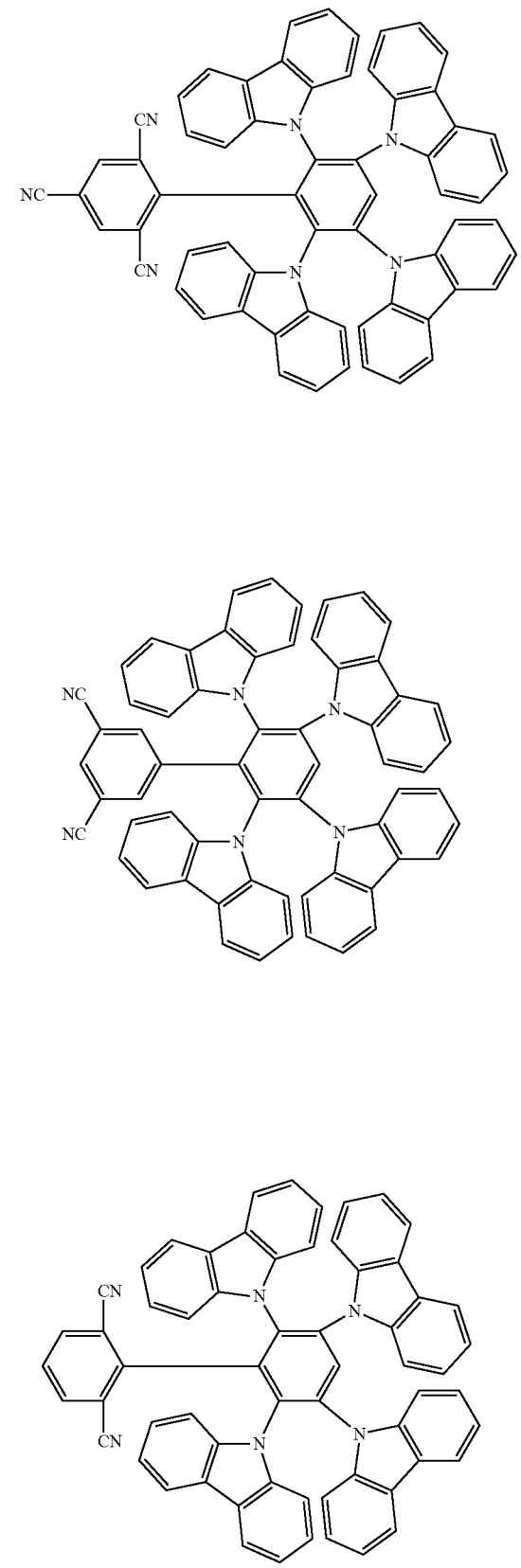

-continued

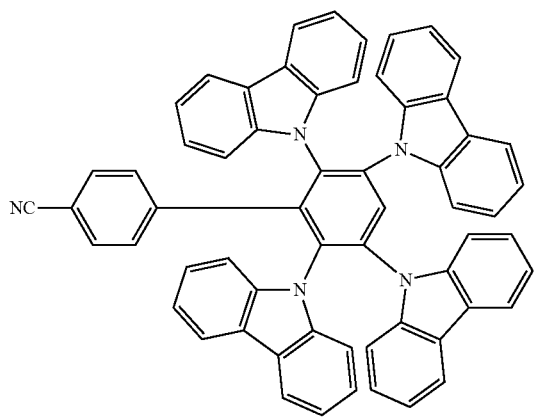

77

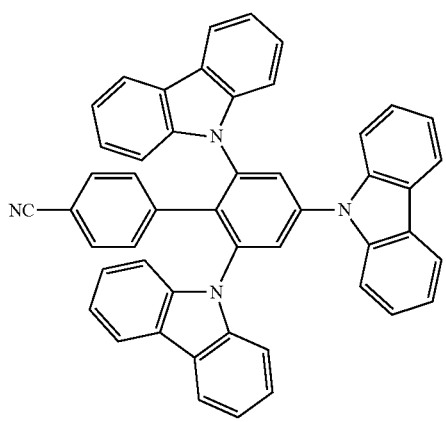

78

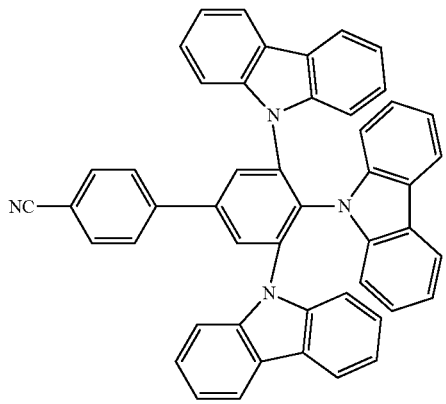

79

In one embodiment, the chemical bond having the curve

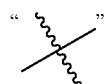

may refer to a broken bond. The broken bond may be able to connect with another broken bond to form a complete chemical bond. The broken bonds may cause two function group to connect according to a general formula. Further, the function group having the broken bonds may directly connect to certain position of a phenyl group.

The disclosed nitrogen-containing heterocyclic compound may be synthesized by any appropriate methods. For illustrative purposes, the synthesis route and the synthesis method of

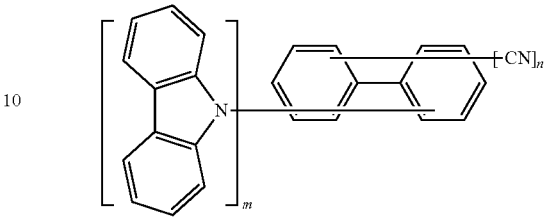

are described as an example, where m and n may be independent integers from 1 to 3; and a sum of m and n may be smaller than 5.

The synthesis route is shown as followings.

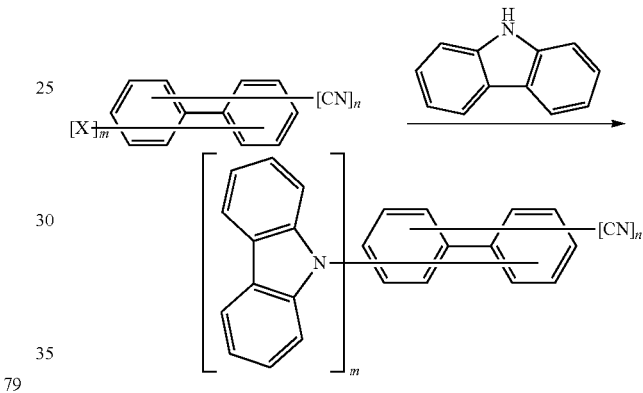

Where X may be F, or Br, etc. m and n may be independently selected from 1 to 3.

When X is F, the synthesis of the nitrogen-containing heterocyclic compound may include following steps. Under an argon protective environment, carbazole (1.2 m eq.) and NaH (1.44 m eq.) may react in dehydrated THF. Then, the product(s) may react with nitrile-containing reactant (1 eq.). After a purification process, the compound may be obtained.

When X is Br, under an argon protective environment, a nitrile-containing reactant (1 eq.), carbazole (1.2 m eq.), CuI (0.1 m eq), $K_3PO_4$ (2 m eq.) and 1,2-Diaminocyclohexane (0.2 m eq.) may react in toluene under an elevated temperature. Then, the product(s) may be purified; and the compound may be obtained.

In certain other embodiments, such a synthesis method may be improved or modified to synthesize other compounds consistent with the disclosed embodiments. For example, carbazole may be substituted (or replaced) by one or more compounds having the general formula (II). That is, a hydrogen atom may be connected to the broken bond. When carzole is substituted by two or more compounds (e.g., a mixture) having the general formula (II), the two or more compound or the mixture may be added by one-step substitution X or multiple-step substitution to substitute X atoms.

According to the disclosed embodiments, the disclosed nitrogen-containing heterocyclic compounds may be applied in organic photoelectric apparatus. The organic photoelectric apparatus may be OLED, photovoltaic devices, organic photoelectric sensors, and organic data storage devices, etc.

Further, according to the disclosed embodiments, an organic photoelectric apparatus is provided. The organic photoelectric apparatus may include an anode layer, a cathode layer, and at least one organic layer formed between the anode layer and the cathode layer. The organic layer may include one or more of the disclosed compounds.

In one embodiment, the organic layer may include a light-emitting layer. The light-emitting layer may include one or more of the disclosed compounds. The disclosed compound may be used as at least one of doping material, co-doping material, and host material, etc.

In one embodiment, the organic layer may also include one or more of a hole-transport layer, a hole injection layer, an electron barrier layer, a hole barrier layer, an electron transport layer, and an electron injection layer, etc.

Definitions

The technical and scientific terms used herein, if not specified, may include ordinary meaning of the terms as known to one of ordinary skill in the art. The terms defined herein may be interpreted according to the present disclosure.

As used herein, unless otherwise specified, the term "alkyl group" refers to completely saturated hydrocarbon (without double bond or triple bond). The alkyl group may be linear alky group or branched alkyl group. The alky group may have 1-30 carbon atoms, 1-20 carbon atoms, 1-10 carbon atoms, and 1-6 carbon atoms, etc. For example, the range 1-30 may include all the integers between 1 and 30 and including 1 and 30, i.e., including 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30. For example, the alky group may be selected from methyl group, ethyl group, propyl group, isopropyl group, n-butyl group, isobutyl group, sec-butyl group, tertbutyl group, pentyl group, and hexyl group, etc. The alkyl group may be substituted alkyl group, or on-substituted alkyl group.

As used herein, unless otherwise specified, the term "aromatic group" refers to carbon rings) having completely localized π-electrons throughout all the rings. The aromatic group may include monocyclic aromatic group or polycyclic aromatic group. The polycyclic aromatic group may be a system having two or more aromatic rings such as two or more benzene rings. The two or more aromatic rings may be bonded by single bond, or condensed by shared chemical bonds. The number of carbon atoms in the aromatic group may vary. For example, the aromatic group may have 6-30 carbon atoms. The range 6-30 may include all the integers between 6 and 30 and including 6 and 30, i.e., including 6, 7, 8, 9, 10, 11, 12, 13, 14, 15, 16, 17, 18, 19, 20, 21, 22, 23, 24, 25, 26, 27, 28, 29, and 30. The exemplary aromatic group may include, but be not limited to, benzene group, biphenyl group, nathpho group, anthryl group, phenanthryl group and pyrenyl group, etc. The aromatic group may be substituted aromatic group or non-substituted aromatic group.

As used herein, unless otherwise specified, the term "heterocyclic aromatic group" refers to a monocyclic or polycyclic aromatic group, having one or more hetero atoms. The hetero atoms may be any element other than carbon. For example, the hetero atoms may include N, O and S, etc. The number of carbon atoms in the heterocyclic aromatic group may vary. For example, the heterocyclic aromatic group may have 1-20 carbon atoms. The range 1-20 may include all the integers between 1 and 20, and including 1 and 20, i.e., including 1, 2, 3, 4, 5, 6, 7, 8, 9, 10, 11, 12, 13, 14, 15, 16, 17, 18, 19 and 20. Further, the heterocyclic aromatic group may have 1-30 ring skeleton atoms. The range 1-30 may include all the integers between 1 and 30 and including 1-30, i.e., including 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30. Further, the term "heterocyclic aromatic group" may include a fused-ring system. In this system, two rings (e.g., at least one aromatic ring and at least one heterocyclic aromatic ring or at least two heterocyclic aromatic rings) may share at least one chemical bond. The exemplary heterocyclic aromatic group may include, but be not limited to, furyl group, furazanyl group, thienyl group, benzothiophenyl group, thalazinyl group, pyrrolyl group, oxazolyl group, benzoxazolyl group, 1,2,3-oxadiazolyl group, 1,2,4-oxadiazolyl group, thiazolyl group, 1,2,3-thiadiazolyl group, 1,2,4-thiadiazolyl group, benzothiazolyl group, imidazolyl group, benzimidazolyl group, indyl group, indazolyl group, pyrazol group, benzopyrazol group, isoxazolyl group, benzisoxazolyl group, isothiazol group, triazolyl group, benzotriazol group, thiadiazolyl group, tetrozolyl group, pyridyl group, pyridazinyl group, pyrimidinyl group, pyrazinyl group, purinyl group, pteridinyl group, quinolyl group, isoquinolyl group, quinazolinyl group, quinoxalinyl group, cinnolinyl group and triazinyl group, etc. The heterocyclic aromatic group may be substituted heterocyclic aromatic group or non-substituted heterocyclic aromatic group.

Organic Photoelectric Apparatus

The disclosed organic photoelectric apparatus may include organic light-emitting diode (OLED), organic solar cell, organic photoelectric sensor and organic data storage apparatus, etc.

An OLED may include an anode, a cathode and one or more organic layers between the anode and the cathode. The one or more organic layers may include at least one light-emitting layer; and the light-emitting layer may include the disclosed compound. The OLED may also include a hole transport layer (HTL), a hole injection layer (HIL), an electron barrier layer (EBL), a hole barrier layer (HBL), an electron transport layer (ETL), an electron injection layer (EIL) and a combination thereof. One or more of such layers may include the disclosed compound. The disclosed compound may be used as one or more of doping material, co-doping material and host material of the light-emitting layer. The light-emitting layer may include two or more disclosed compounds.

When the light-emitting layer includes two materials, the mass percentile of the first material may be in a range of approximately 0%-50% but not include 0. The first material may be used to emit light after being electrically activated. Thus, the first material may be referred to as a doping material. The mass percentile of the second material may be in a range of 100%-50% but not include 100%. Holes from the anode and electrons from the cathode may recombine to generate excitons in the second material; and the excitons may be transported to the doping material by the second material. Thus, the second material may be referred to as a host material.

When the light-emitting layer includes the first material and the second material, the mass percentile of the first material and the second material may all be in a range of 0%-50% but not include 0. The first material may emit light after being activated; and may be referred to as a doping material. The other one or more material may be used to transport the exciton energy to the doping material; and may be referred to as a co-doping material. Except such materials, the remaining one or more materials may have a mass percentile or a total mass percentile in a range of approximately 100%-50% but not include 100%. Such remaining one or more materials may be used to transport excitons generated by the recombination of the electrons from the cathode and the holes from the anode to the doping material and the co-doping material; and may be referred as to a host material. The mass percentiles of the doping material, the co-doping material and the host material may be any other appropriate values.

For illustrative purposes, OLED structures are described as examples of the organic photoelectric apparatus utilizing the disclosed compounds. FIGS. 1-5 illustrate exemplary OLED structures consistent with the disclosed embodiments.

As shown in FIGS. 1-5, the OLED utilizing the disclosed compounds may include a substrate layer 100, and an anode layer 110 formed over the substrate layer 100. The anode layer 110 and the substrate layer 100 may be referred as an anode substrate. The OLED may also include at least a light-emitting layer 130 formed over the anode layer 110, and a cathode layer 120 formed over the light-emitting layer 130. That is, the light-emitting layer 130 may be in between the anode layer 110 and the cathode layer 120.

Figure 2:
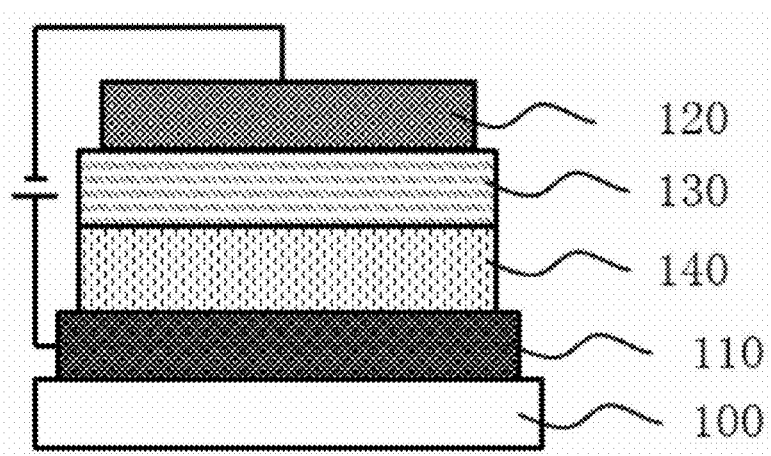
FIG. 2 illustrates another exemplary OLED consistent with the disclosed embodiments.

In one embodiment, as shown in FIG. 1, the anode layer 110 and the cathode layer 120 of the OLED may only have the light-emitting layer 130 there-between. The electrons and holes may recombine to activate the light-emitting layer 130 to emit light. The light-emitting layer 130 may be made of one or more of the disclosed compounds In certain other embodiments, as shown in FIG. 2, a hole transport layer (HTL) 140 may be formed between the light-emitting layer 130 and the anode layer 110. That is, the HTL 140 and the light-emitting layer 130 are in between the anode layer 110 and the cathode layer 120 of the OLED. The HTL 140 may transport the holes to the light-emitting layer 130. The light-emitting layer 130 may be made of one or more of the disclosed compounds.

Figure 3:
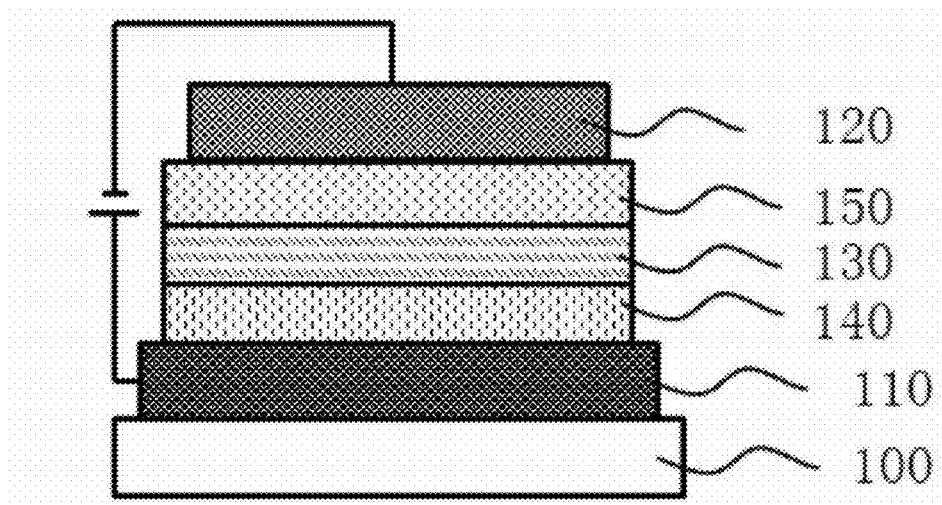
FIG. 3 illustrates another exemplary OLED consistent with the disclosed embodiments.

In still certain other embodiments, as shown in FIG. 3, an electron transport layer (ETL) 150 may be formed between the cathode layer 120 and the light-emitting layer 130. That is, the HTL 140, the light-emitting layer 130 and the ETL 150 may be in between the anode layer 120 and the cathode layer 110. The ETL 150 may transport electrons to the light-emitting layer 130. The light-emitting layer 130 may be made of one or more of the disclosed compounds.

Figure 4:
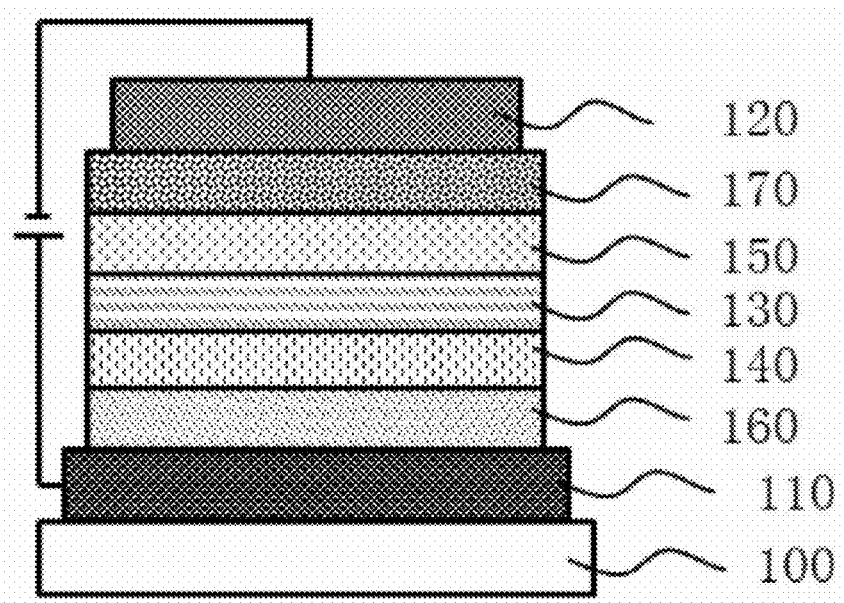
FIG. 4 illustrates another exemplary OLED consistent with the disclosed embodiments.

In still certain other embodiments, as shown in FIG. 4, a hole injection layer (HIL) 160 may be formed between the anode layer 110 and the HTL 140; and an electron injection layer (EIL) 170 may be formed between the cathode layer 120 and the ETL 150. That is, the HIL 160, the HTL 140, the light-emitting layer 130, the ETL 150 and the ETL 170 may be in between the anode layer 110 and the cathode layer 120. The HIL 160 may be able to improve the ability to transport the holes from the anode layer 110 to the light-emitting layer 130. The EIL 170 may be able to improve the ability to transport the electrons from the cathode layer 120 to the light-emitting layer 130. Accordingly, the drive voltage of the OLED may be reduced. The light-emitting layer 130 may be made of one or more of the disclosed compounds.

Figure 5:
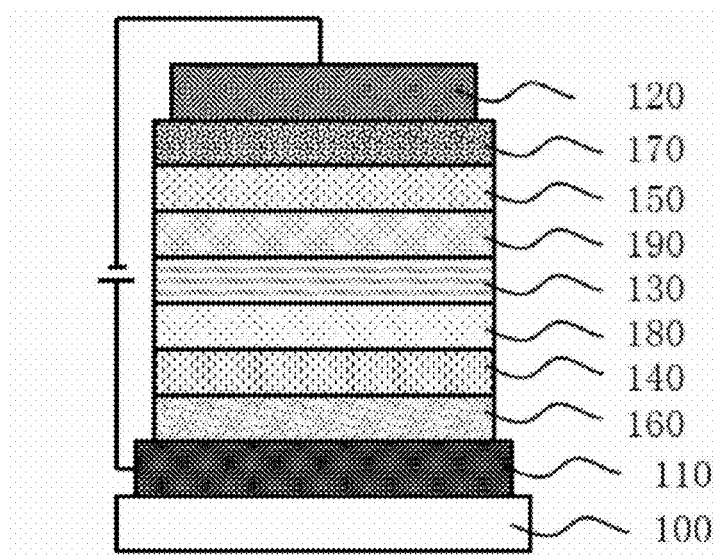
FIG. 5 illustrates another exemplary OLED consistent with the disclosed embodiments.

In still certain other embodiments, as shown in FIG. 5, an electron barrier layer (EBL) 180 may be formed between the light-emitting layer 130 and the HTL 140; and a hole barrier layer (HBL) 190 may be formed between the light-emitting layer 130 and the ETL 150. That is, the HIL 160, the HTL 140, the EBL 180, the light-emitting layer 130, the HBL 190, the ETL 150 and the ETL 170 may be in between the anode layer 110 and the cathode layer 120. The EBL 180 may be able to prevent electrons from entering into the HTL 140 from the light-emitting layer 130; and the HBL 190 may be able to prevent the holes from entering into the ETL 150 from the light-emitting layer 130. The light-emitting layer 130 may be made of one or more of the disclosed compounds.

The anode layer 110 may be made of any appropriate material with a relatively large work function. The material used for the anode layer 110 may include Cu, Au, Ag, Fe, Cr, Ni, Mn, Pd, Pt, or a combination thereof. The material used for the anode layer 110 may also be metal oxide, such as SnO, ZnO, ITO, IZO, or a combination thereof. Further, the material used for the anode layer 110 may also be a conductive polymer, such as polyaniline, polypyrrole, poly (3-methylthiophene), or a combination thereof. In one embodiment, the anode layer 110 is made of ITO.

The cathode layer 120 may be made of any appropriate material with a relatively small work function, such as Al, Mg, Ag, In, Sn, Ti, Ca, Na, K, Li, Yb, Pb, or a combination thereof. The cathode layer 120 may also be made of a multiple-layer material, such as LiF/Al, or Liq(8-quinolinol), etc. In one embodiment, an alloy of Mg and Ag or a double layer structure of LiF/Al may be used as the material of the cathode layer 120.

The HIL 160 may be made of any appropriate material such that the injection of holes from the anode layer 110 to the organic interface layer may be increased, and the HIL 160 may have a desired adhesion to the surface of the ITO anode 110. The material used for the HTL 160 may include the polymers with the HOMO energy level matching the work function of ITO, such as porphyrin compounds of CuPc, naphthylenediamine-containing stellate triphenylamine derivatives of 4,4',4"-tris[2-naphthyl-phenyl-amino]triphenylamine (TNATA) and poly(3,4-Ethylenedioxythiophene):polystyrene sulfonate (PEDOT:PSS), and electron withdrawing nitrogen-containing heterocyclic compounds of Hexaazatriphenylenehexacabonitrile (HATCN), etc.

The HTL 140 and the EBL 180 may be may made of any appropriate material having a relatively high glass transition temperature and a high hole mobility. The material used for the HTL 140 and EBL 180 may include the diphenyl diamine derivatives of N,N'-Di-[(1-naphthalenyl)-N,N'-diphenyl]-1,1'-biphenyl)-4,4'-diamine (NPD), the crossing diphenyl diamine derivatives of 2',7,7'-tetrakis(N,N-diphenylamino)-9,9-spirobifluorene (spiro-TAD), and the stellate triphenylamine derivatives of 4,4',4"-Tris(carbazol-9-yl)triphenylamine (TCTA), etc.

The HBL 190 and the ETL 150 may be made any appropriate material having a relatively low HOMO energy level, and a relatively high electron mobility. The material used for the HBL 190 and ETL 150 may include the metal-quinolinolatocomplexs of bis(2-methyl-8-quinolinolato-N1,O8)-(1,1'-Biphenyl-4-olato)aluminum (BAlq), tris (8-hydroxyquinolinato)aluminum (Alq), 8-hydroxyquionline lithium, the phenanthroline derivatives of 4,7-diphenyl-1,10-phenanthroline (BPhen), the imidazoline derivatives of 1,3,5-Tris(1-phenyl-1H-benzimidazol-2-yl)benzene (TPBI), or the triazine derivatives of 2,4,6-Tri(9H-carbazol-9-yl)-1, 3,5-triazine, etc.

The OLED having the disclosed compound may be formed by any appropriate methods. In one embodiment, the method for forming the OLED may include forming an anode layer on a smooth transparent or opaque substrate; forming an organic layer made of at least one of the disclosed compounds over the anode layer; and forming a cathode layer over the organic layer. The organic layer may be formed by any appropriate process, such as a thermal evaporation process, a sputtering process, a spin-coating process, a dip-coating process, or an ion deposition process, etc.

The following embodiments will further describe the advantages of the disclosed compounds and OLEDs having the disclosed compounds. Exemplary embodiments 1-10 describe the simulation process of exemplary compounds consistent with the disclosed embodiments.

The energy level different of the minimum singlet stage $S_1$ and the minimum triplet stage $T_1$ of an organic material may be simulated by Guassian 09 software (Guassian Inc.). The detailed simulation method of the energy level difference $\Delta E_{st}$ may refer to J. Chem. Theory Comput., 2013, DOI: 10.1021/ct400415r. The optimization of the molecular structure and the activation may all be obtained by TD-DFT method "B3LYP" and base group "6-31g(d)".

In embodiment 1, a simulation process is performed on the compound 1.

In embodiment 2, a simulation process is performed on the compound 2.

In embodiment 3, a simulation process is performed on the compound 7.

In embodiment 4, a simulation process is performed on the compound 14.

In embodiment 5, a simulation process is performed on the compound 21.

In embodiment 6, a simulation process is performed on the compound 33.

In embodiment 7, a simulation process is performed on the compound 36.

In embodiment 8, a simulation process is performed on the compound 38.

In embodiment 9, a simulation process is performed on the compound 50.

In embodiment 10, a simulation process is performed on the compound 66.

The simulation results are illustrated in Table 1.

TABLE 1

| | Compound | $S_1$ (eV) | $T_1$ (eV) | $\Delta E_{st}$ (eV) |
|---|---|---|---|---|
| Embodiment 1 | 1 | 3.09 | 2.98 | 0.11 |
| Embodiment 2 | 2 | 3.01 | 2.71 | 0.30 |
| Embodiment 3 | 7 | 3.17 | 2.93 | 0.24 |
| Embodiment 4 | 14 | 2.94 | 2.81 | 0.13 |
| Embodiment 5 | 21 | 2.70 | 2.62 | 0.08 |
| Embodiment 6 | 33 | 2.66 | 2.50 | 0.16 |
| Embodiment 7 | 36 | 2.46 | 2.38 | 0.08 |
| Embodiment 8 | 38 | 2.23 | 2.12 | 0.11 |
| Embodiment 9 | 50 | 3.20 | 2.92 | 0.28 |
| Embodiment 10 | 66 | 3.00 | 2.78 | 0.22 |

As shown in Table 1, the energy level difference $\Delta E_{st}$ between the minimum single stage $S_1$ and the triplet state $T_1$ may all be relatively small, from the embodiment 1 to the embodiment 10. Thus, the compounds in Table 1 may all be able to achieve a reverse intersystem crossing; and may have the performances of the TADF materials.

Embodiments 11-15 describe exemplary synthesis routes of the disclosed compounds consistent with the disclosed embodiments.

Embodiment 11 describes the synthesis route and synthesis process of the compound 1. The synthesis route is illustrated as follows.

The first step of the synthesis process of the compound 1 may be to synthesize the intermediated 1-a illustrated in the following synthesis route.

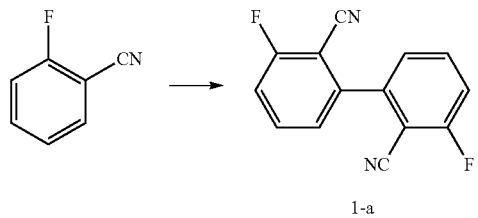

Specifically, under a dry Ar gas, 2-fluorobenzonitrile (1.2 g, 10.0 mmol) may be dissolved in 50 ml dehydrated THF. Then, the THF solution of $(2,2,6,6\text{-tetramethylpiperidyl})_2$ $Mn\cdot 2MgCl_2\cdot 4LiCl$ (6.0 mmol) may be slowly dropped in to the 2-fluorobenzonitrile solution; and stirred for 1 hour in an ice bath. Then, an appropriate amount of $I_2$ may be added into the solution to quench the residual reactants. At $-20°$ C., chloranil (2.5 g, 10.0 mmol) may be added into the mixture; and stirred for 1 hour. Then, a saturated $NH_4Cl$ solution may be added to quench the reaction. Dichloromethane may be used to extract the organic phases from the products. The organic phases may be combined; and dried by dehydrated $MgSO_4$. The product may be then purified by a silicone gel chromatographic column. Thus, the intermediate 1-a (0.8 g, yield 63%) may be obtained.

The second step of the synthesis process of the compound 1 may be to synthesize the final compound 1 illustrated in the following synthesis route.

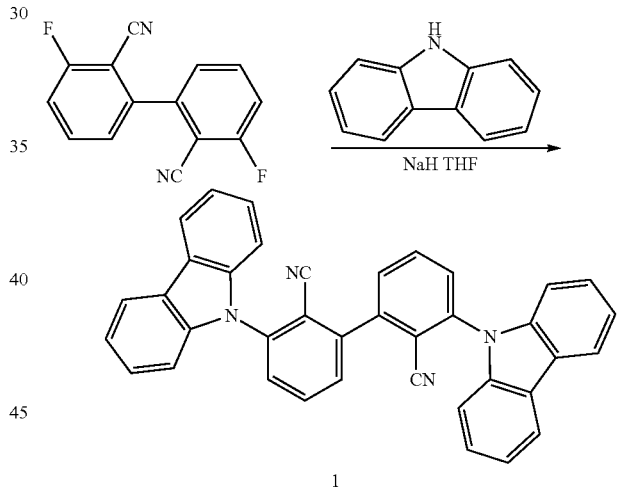

Specifically, under an Ar gas, the 60% NaH (0.36 g, 9.1 mmol) may be washed by dehydrated hexane; and added into a dehydrated THF solution of carbazole (1.3 g, 7.6 mmol). The reaction may continue for 1 hour. Then, the dehydrated THF of the intermediate 1-a (0.8 g, 3.2 mmol) may be added into the mixture; and the reaction may continue for 12 hours. Then, the reaction may be quenched by water. Dichloromethane may be used to extract the organic phases from the products. The organic phases may be combined; and dried by dehydrated $MgSO_4$. The product may be then purified by a silicone gel chromatographic column. Thus, the compound 1 (0.4 g, yield 25%) may be obtained An LC-MS method may be used to analyze the final product (the obtained compound 1). The ESI-MS (m/z) of the final product is approximately 535.1 $[M+H]^+$. Such a value corresponds to the molecular weight of the compound 1.

Embodiment 12 describes the synthesis route and the synthesis process of the compound 2. The first step of the synthesis process of the compound 2 may be to synthesize the intermediate 2-a illustrated in the following synthesis route.

Specifically, 1,4-dibromo-2-nitrobenzene (5.6 g, 20.0 mmol) may be dissolved in 50 ml DMF; and Cu powder (2.8 g, 44.0 mmol) may be added into the solution. The mixture may be heated to 120° C. to react for 3 hours. The reaction product may be cooled down to the room temperature. After being filtered and extracted by toluene, and dried by dehydrated $MgSO_4$, the recrystallized solid may be dissolved into a mixture of HCl and ethanol. Then, Sn power (1.0 g) may be added into the mixture, and reactants may be refluxed for 2 hours. After the reaction finishes, ice may be added into the reactants; and NaOH solution may be added to neutralize the mixture. Dichloromethane may be used to extract the organic phases from the products. The organic phases may be combined; and dried by dehydrated MgSO4. The product may be then purified by a silicone gel chromatographic column. Thus, the intermediate 2-a (2.4 g, yield 71%) may be obtained The second step of the synthesis process of the compound 2 may be to synthesize the intermediate 2-b illustrated in the following synthesis route.

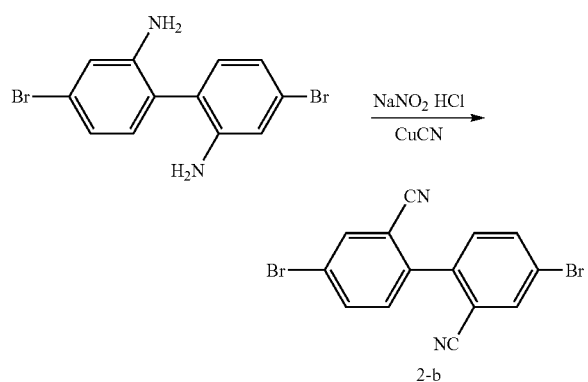

The intermediate 2-a (2.4 g, 7.0 mmol) may be dissolved in acetic acid. In an ice bath, 15 ml HCl and $NaNO_2$ may be slowly added into the solution. After bubbles are generated in the solution, CuCN (2.8 g, 31.5 mmol) may be added into the solution; and the solution may be stirred for 1 hour. Then, the product(s) may be stirred for 3 hours at 60° C. Then, ammonia may be added into the solution; and the separated out solid may be filtered out; and may be purified by a silicone gel chromatographic column. Thus, the intermediate 2-b (1.2 g, 47%) may be obtained.

The third step of the synthesis process of the compound 2 may be to synthesize the final compound 2 illustrated in the following synthesis route.

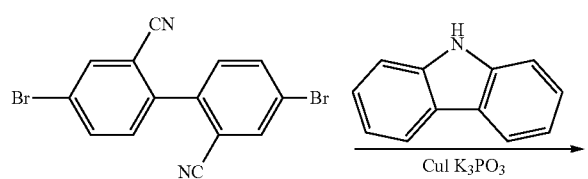

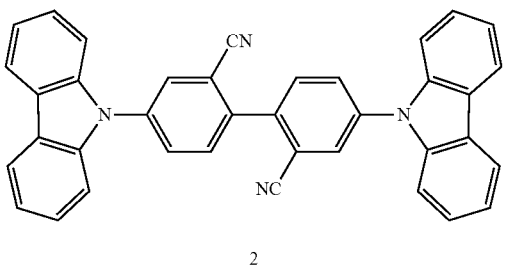

Specifically, the intermediate 2-b (1.2 g, 3.3 mmol), carbazole (1.3 g, 7.9 mmol, CuI (0.13 g, 0.7 mmol), 1,2-diaminocyclohexane (0.14 g, 1.3 mmol) and $K_3PO_3$ (2.8 g, 13.2 mmol) may be added into a reaction flask. Under an Argon gas, 50 ml toluene may be added into the reaction flux to dissolve the precursors under a stirring. The reaction in the reaction flask may continue for 1 day at 110° C. The temperature of the reaction may be cooled down to the room temperature, diluted HCl may be used to quench the residual precursors. Then, the organic phases may be extracted by dichloromethane; and the extracted organic phases may be combined; and washed by ammonia. The washed organic phases may be dried by dehydrated $MgSO_4$; and purified by a silicone gel chromatographic column. Thus, the white compound 2 (0.7 g, yield 38%) may be obtained.

An LC-MS method may be used to analyze the final product (the obtained compound 2). The ESI-MS (m/z) of the final product is approximately 535.1 $[M+H]^+$. Such a value corresponds to the molecular weight of the compound 2.

Embodiment 13 describes the synthesis route and synthesis process of the compound 7.

The first step of the synthesis process of the compound 7 may be to synthesize the intermediate 7-a illustrated in the following synthesis route. The intermediate 7-a may be synthesized by any appropriate process.

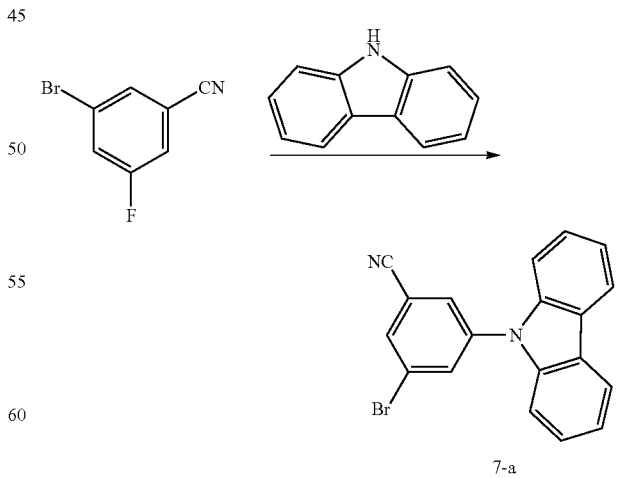

The second step of the synthesis process of the compound 7 may be to synthesize the intermediate 7-b illustrated in the following synthesis route.

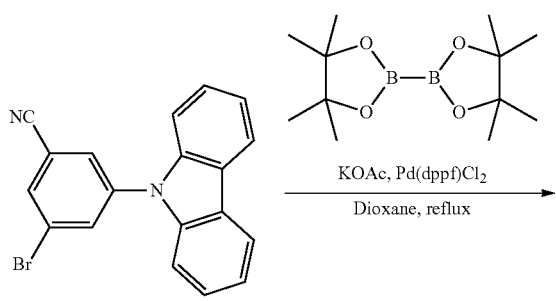

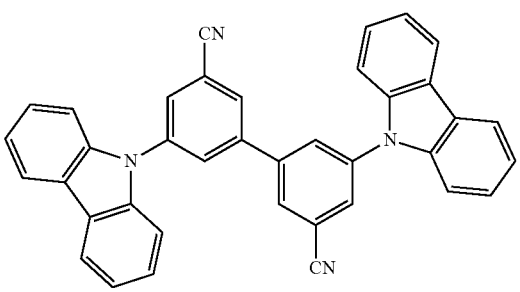

7

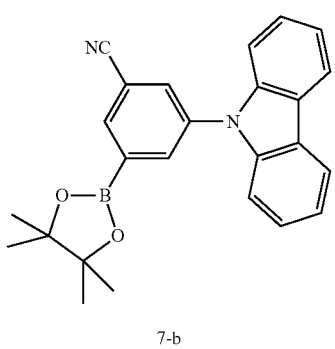

7-b

Under a N₂ flow, the catalyst Pd(dppf)₂ (0.2 g, 0.3 mmol), KOAc (0.3 g, 3.5 mmol), and bis(pinacolato)diboron (2.8 g, 11.0 mmol) may be added into a reaction flask. The intermediate 7-a (3.5 g, 10.0 mmol) may be dissolved in 300 ml 1,4-dioxane; and added into the reaction flask. The reaction may be refluxed for 10 hours. After being cooling down, an extraction process may be performed using toluene. The organic layer may be washed by water for a plurality of times; and dried by dehydrated MgSO₄. After filtering and evaporating the solvent, the intermediate 7-b (1.9 g, yield 49%) may be obtained.

The third step of the synthesis process of the compound 7 may be to synthesize the final compound 7 illustrated in the following synthesis route.

Under an Ar gas flow, the intermediate 7-b (1.9 g, 4.9 mmol), the intermediate 7-a (1.5 g, 4.5 mmol), the catalyst Pd(dppf)Cl₂ (0.07 g, 0.1 mmol), and 20 ml 2M Na₂CO₃ may be mixed in 100 ml toluene; and may be refluxed for 10 hours. After cooling down, dichloromethane may be added to perform an extraction process. Then, the obtained organic phases may be washed by water for a plurality of times; and dried by dehydrated MgSO₄. The organic phased may be filtered; and purified by a silicone gel chromatographic column. Thus, the solid compound 7 (0.9 g, yield 38%) may be obtained.

An LC-MS method may be used to analyze the final product (the obtained compound 7). The ESI-MS (m/z) of the final product is approximately 535.1 $[M+H]^+$. Such a value corresponds to the molecular weight of the compound 7.

Embodiment 14 describes the synthesis route and synthesis process of the compound 14.

The first step of the synthesis process of the compound 7 may be to synthesize the intermediate 14-a illustrated in the following synthesis route.

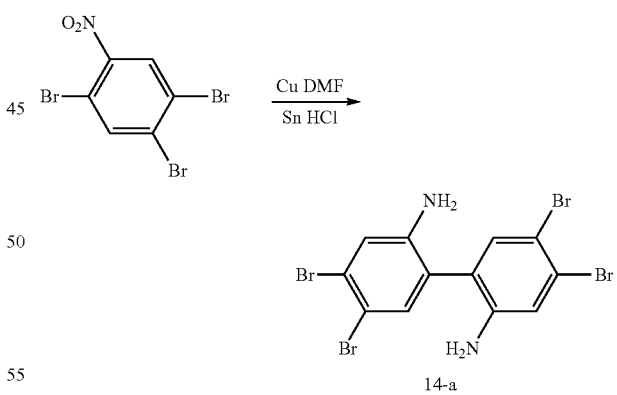

14-a

The intermediate 14-a may be synthesized by a process similar to that of the intermediate 2-a, except that the 1,4-dibromo-2-nitrobenzene may be substituted by 1-nitro-1,3,4-tribromobenzene (7.2 g, 20.0 mmol). After the synthesis process, the intermediate 14-a (3.2 g, yield 64%) may be obtained.

The second step of the synthesis process of the compound 14 may be to synthesize the intermediate 14-b illustrated in the following synthesis route.

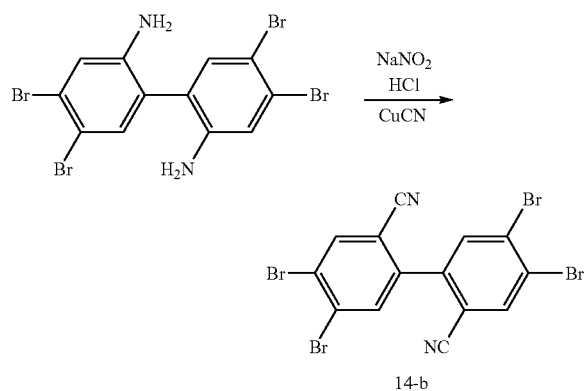

14-b

The synthesis process of the intermediate 14-b may be similar to that of the intermediate 2-b, except the intermediate 2-a may be substituted by the intermediate 14-a. After the synthesis process, the intermediate 14-b (1.7 g, 51%) may be obtained.

The third step of the synthesis process of the compound 14 may be to synthesize the final compound 14 illustrated in the following synthesis route.

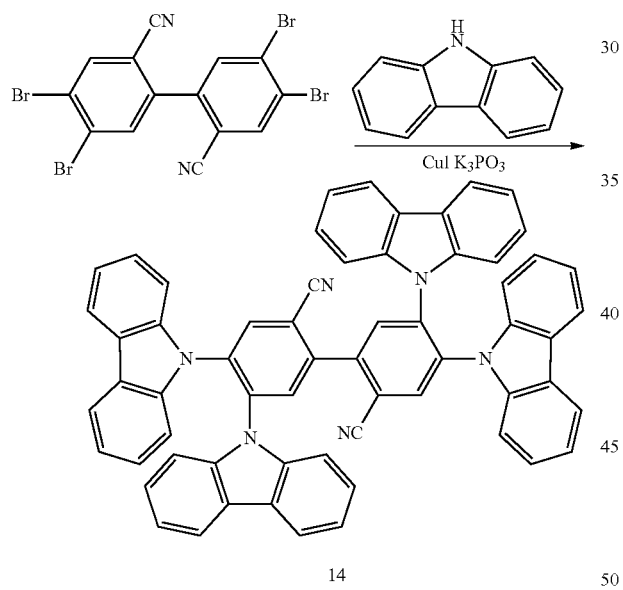

14

The synthesis process of the final compound 14 may be similar to that of the final compound 2, except the intermediate 2-b may be substituted by the intermediate 14-b. After the synthesis process, the final compound 14 (0.7 g, 31%) may be obtained.

An LC-MS method may be used to analyze the final product (the obtained compound 14). The ESI-MS (m/z) of the final product is approximately 865.1 [M+H]$^+$. Such a value corresponds to the compound 14.

Embodiment 15 describes the synthesis route and the synthesis process of the compound 50. The first step of the synthesis process of the compound 50 may be to synthesize the intermediate 2-a illustrated in the following synthesis route.

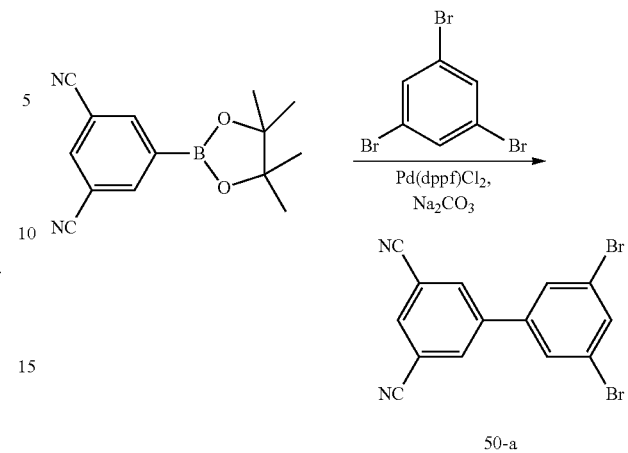

50-a

Specifically, under an Ar gas flow, 4,4,5,5-tetramethyl-1,3,2-dioxaborolan-1,3-dicyanobenzene (2.5 g, 10.0 mmol), tribromobenzene (3.3 g, 10.0 mmol), Pd(dppf)Cl$_2$ (0.15 g, 0.2 mmol) and 40 ml 2M Na$_2$CO$_2$ water solution may be mixed in 200 ml toluene; and refluxed overnight. After being cooled to the room temperature, the organic phases may be extracted by dichloromethane. The organic phases may be washed by water for a plurality of times; and dried by dehydrated MgSO4. After being filtered, and evaporating the solvent, the product(s) may be purified by a silicone gel chromatographic column. Thus, the intermediate 50-a (1.7 g, yield 47%) may be obtained The second step of the synthesis process of the compound 50 may be to synthesize the final compound 50 illustrated in the following synthesis route.

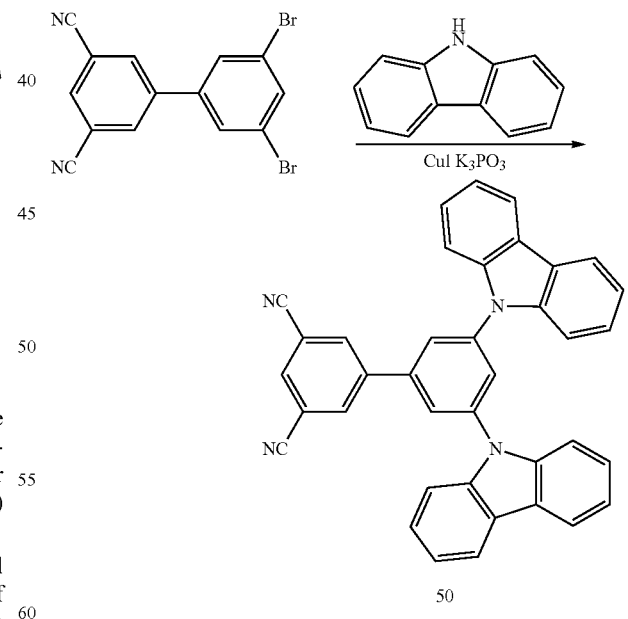

50

Specifically, the intermediate 50-a (1.7 g, 4.7 mmol), carbazole (1.9 g, 11.3 mmol, CuI (0.17 g, 0.9 mmol), 1,2-diaminocyclohexane (0.22 g, 1.9 mmol) and K$_3$PO$_3$ (4.0 g, 18.8 mmol) may be added into a reaction flask. Under an Argon gas, 100 ml toluene may be added into the reaction flask to dissolve the precursors under stirring. The reaction in the reaction flask may continue for 1 day at 110° C. After the temperature of the reaction cools down to the room temperature, diluted HCl may be used to quench the residual precursors. Then, the organic phases may be extracted by dichloromethane; and the extracted organic phases may be combined; and washed by ammonia. The washed organic phases may be dried by dehydrated MgSO$_4$ and purified by a silicone gel chromatographic column. Thus, the final compound 50 (0.8 g, yield 31%) may be obtained.

An LC-MS method may be used to analyze the final product (the obtained compound 50). The ESI-MS (m/z) of the final product is approximately 535.1 [M+H]$^+$. Such a value corresponds to the molecular weight of the compound 50.

Figure 6:
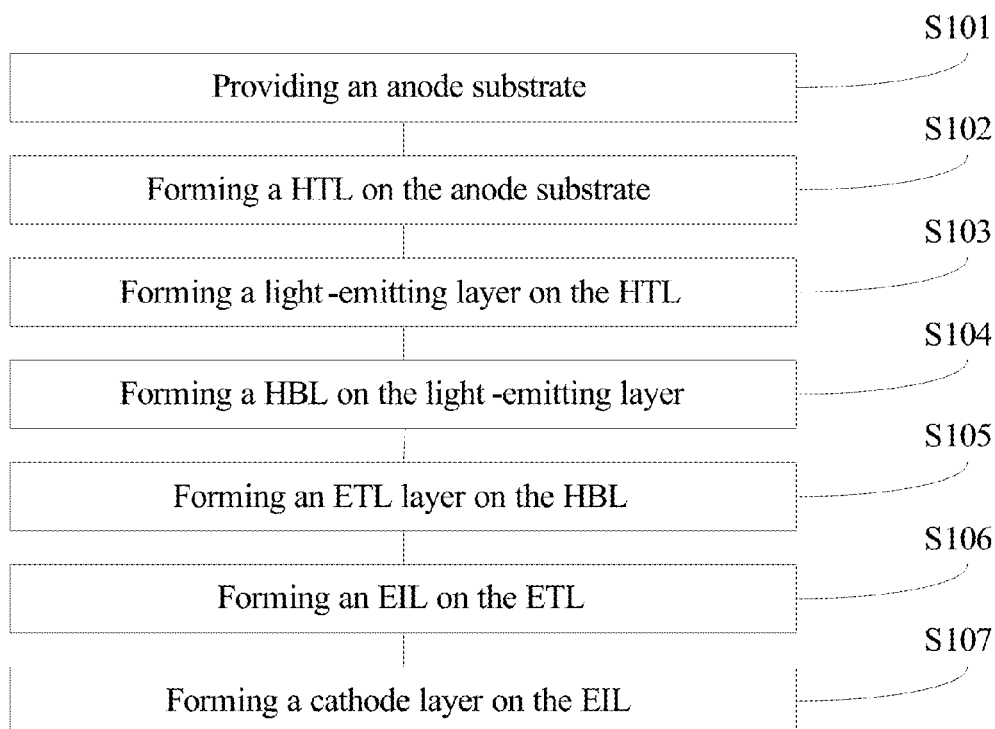
FIG. 6 illustrate an exemplary fabrication process of an organic photoelectric apparatus consistent with the disclosed embodiments.

FIG. 6 illustrates an exemplary fabrication process of the photoelectric apparatus having the disclosed compound consistent with the disclosed embodiments. Embodiments 16-25 detailed descriptions exemplary fabrication processes of organic photoelectric apparatus consistent with the disclosed embodiments. Control embodiments 1-2 describe fabrication processes of two control organic photoelectric apparatus.

FIG. 6 illustrates an exemplary fabrication process of the organic photoelectric apparatus having the disclosed compound. As shown in FIG. 6, the method includes providing an anode substrate (S101); forming a HTL on the anode substrate (S102); forming a light-emitting layer on the HTL using at least one disclosed compound (S103); forming a HBL on the light-emitting layer (S104); forming an ETL on the HBL (S105); forming an EIL on the ETL (S106); and forming a cathode layer on the EIL (S107). For illustrative purposes, the disclosed compound will be used as the host material of one or more of the organic layers in the embodiments 26-32; and used as co-doping material in the embodiments 33-36.

Specifically, in the embodiment 16, an anode substrate having an ITO film with a thickness of 100 nm may be provided. The anode substrate having the ITO film may be sequentially cleaned by DI water, acetone and isopropanol alcohol in an ultrasound bath; and may be put into an oven. After a 30 minute surface treatment, the cleaned anode substrate may be transferred to a vacuum evaporation chamber. the photoelectric apparatus having a plurality of layers may be deposited at a pressure of 2×10$^{-6}$ Pa. An N,N'-bis-(1-naphthalenyl)-N,N'-bis-phenyl-(1,1'-biphenyl)-4,4'-di-amine (a-NPD) layer with a thickness of 60 nm may be deposited on the ITO film; and a 4,4',4''-tris(carbazol-9-yl)-triphenylamine (TCTA) layer with a thickness of 10 nm may be deposited on the NPD layer. The NPD layer and the TCTA layer may form the HTL. Further, the light-emitting layer with a thickness of 30 nm may be deposited on the HTL. The light-emitting layer may include the disclosed compound 1 as the host material (94 wt %) and Ir(ppy)$_3$ as the blue phosphorescence doping material (6 wt %). The host material and the doping material may be deposited simultaneously. Further, abis(2-methyl-8-quinolinolato-N1, O8)-(1,1'-Biphenyl-4-olato)aluminum (BAlq) layer with a thickness of 5 nm may be deposited on the light-emitting layer to be used as the HBL. Then, a 4,7-diphenyl-1,10-phenanthroline (BPhen) layer with a thickness of 20 nm may be deposited on the HBL to be used as the ETL. Then, a LiF layer with a thickness of 1 nm may be deposited on the ETL to be used as the EIL. Then, an Al layer with a thickness of the 100 nm may be deposited on the EIL to be used as a cathode layer. Thus, the organic photoelectric apparatus may have a structure of ITO (100 nm)/NPD (60 nm)/TCTA (10 nm)/Ir(ppy)$_3$:1 (6 wt %, 30 nm)/BAlq (5 nm)/Bphen (20 nm)/LiF (1 nm)/Al (100 nm).

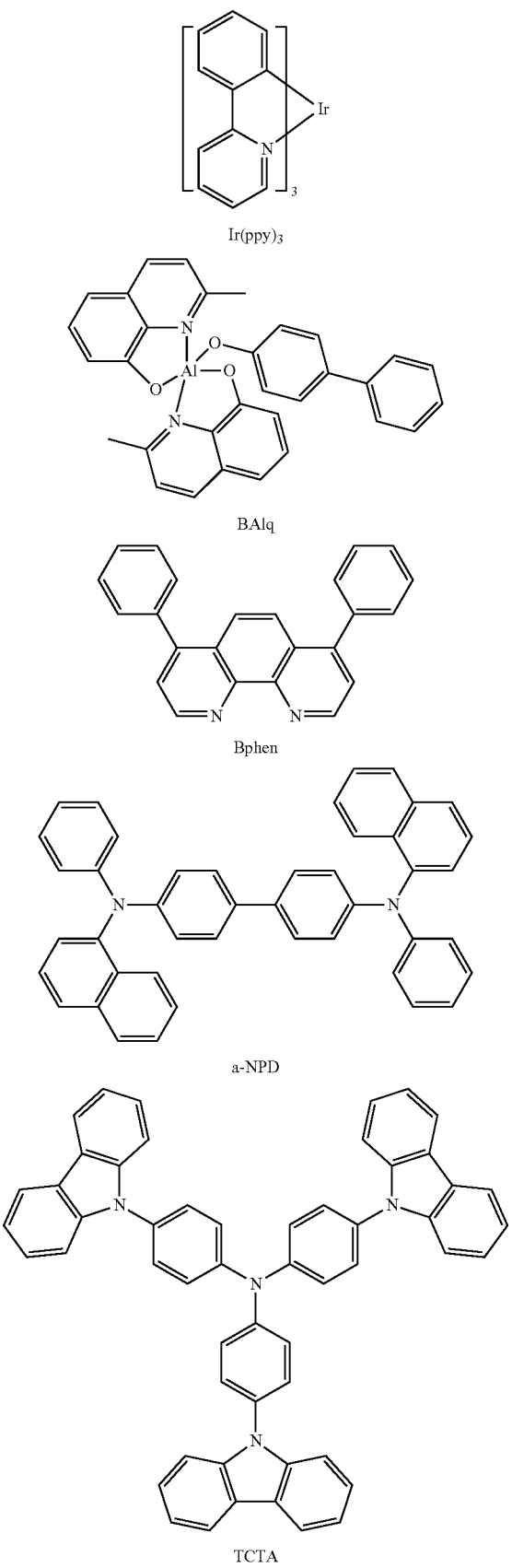

In the embodiment 17, the disclosed compound 2 may be used to substitute the compound 1 described in the embodiment 16 as the host material. Other structures and steps may be similar to those described in the embodiment 16.

In the embodiment 18, the disclosed compound 7 may be used to substitute the compound 1 described in the embodiment 16 as the host material. Other structures and steps may be similar to those described in the embodiment 16.

In the embodiment 19, the disclosed compound 14 may be used to substitute the compound 1 described in the embodiment 16 as the host material. Other structures and steps may be similar to those described in the embodiment 16.

In the embodiment 20, the disclosed compound 50 may be used to substitute the compound 1 described in the embodiment 16 as the host material. Other structures and steps may be similar to those described in the embodiment 16.

In the control embodiment 1, the following compound CBP is used to substitute the compound 1 described in the embodiment 16 as the host material. Other structures and steps may be similar to those described in the embodiment 16.

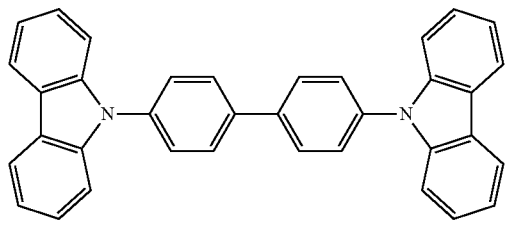

CBP

In the embodiment 21, compound TBPe (1 wt %) may be used as the doping material; and the disclosed compound 1 (15 wt %) may be used as a co-doping material. Compound DPEPO (84 wt %) may be used as the host material. The compound TBPe, the disclosed compound 1 and the compound DPEPO may be deposited simultaneously to be used as the light-emitting layer with a thickness of 30 nm. Other structures and steps may be similar to those described in the embodiment 16.

That is, the organic photoelectric apparatus may have a structure of ITO (100 nm)/NPD (60 nm)/TCTA (10 nm)/TBPe:1:DPEPO (1 wt %:15%, 30 nm)/BAlq (5 nm)/Bphen (20 nm)/LiF (1 nm)/Al (100 nm).

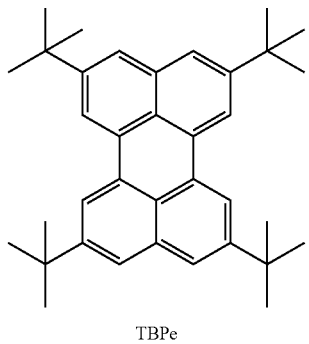

TBPe

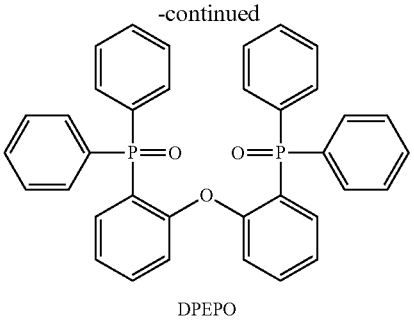

DPEPO

In the embodiment 22, the disclosed compound 2 may be used to substitute the compound 1 described in the embodiment 21 as the co-doping material. Other structures and steps may be similar to those described in the embodiment 21.

In the embodiment 23, the disclosed compound 7 may be used to substitute the compound 1 described in the embodiment 21 as the co-doping material. Other structures and steps may be similar to those described in the embodiment 21.

In the embodiment 24, the disclosed compound 14 may be used to substitute the compound 1 described in the embodiment 21 as the co-doping material. Other structures and steps may be similar to those described in the embodiment 21.

In the embodiment 25, the disclosed compound 50 may be used to substitute the compound 1 described in the embodiment 21 as the co-doping material. Other structures and steps may be similar to those described in the embodiment 21

In the control embodiment 2, TBPe (1 wt %) is used as the doping material; and DPEPO is used as the host material. TBPe and DPEPO are deposited simultaneously to be used as the light-emitting layer with a thickness of 30 nm. Other structures and steps may be similar to those described in the embodiment 21

The performance of the photoelectric apparatus described in the embodiments 16-25 and the control embodiments 1-2 may be evaluated from any aspects, and by any appropriate methods.

In one embodiment, the current of the photoelectric apparatus described in the embodiments 16-25 and the control embodiments 1-2 varying with the voltage is measured by a Keithley 2365 nanovoltagemeter. The current densities of the organic photoelectric apparatus at different voltages are obtained by dividing the current with the light-emitting area.

The brightness and the radiant energy flow density of the photoelectric apparatus described in the embodiments 16-25 and the control embodiments 1-2 at different voltages may be measured by a Konicaminolta CS 2000 Spectroradiometer. According to the brightness and the radiant energy of the photoelectric apparatus at different voltages, the current efficiency (Cd/A) and the external quantum efficiency EQE at a same current density (10 mA/cm$^2$) may be obtained.

The testing results of the photoelectric apparatus described in embodiments 16-20 and the control embodiment 1 are illustrated in Table 2. The testing results of the photoelectric apparatus described in embodiments 21-25 and the control embodiment 2 are illustrated in Table 3.

TABLE 2

Testing results corresponding to different host materials

| | Voltage (V) | Current efficiency (Cd/A) | EQE | CIE |
|---|---|---|---|---|
| Embodiment 16 | 4.0 | 47.3 | 18.7 | Green |
| Embodiment 17 | 4.7 | 42.1 | 16.1 | Green |
| Embodiment 18 | 4.5 | 45.3 | 16.5 | Green |
| Embodiment 19 | 4.2 | 46.1 | 17.7 | Green |
| Embodiment 20 | 4.6 | 43.7 | 16.3 | Green |
| Control embodiment 1 | 5.1 | 40.3 | 15.6 | Green |

TABLE 3

Testing results corresponding to different co-doping materials

| | Voltage (V) | Current efficiency (Cd/A) | EQE | CIE |
|---|---|---|---|---|
| Embodiment 21 | 7.3 | 4.1 | 2.5 | Blue |
| Embodiment 22 | 7.7 | 3.2 | 1.9 | Blue |
| Embodiment 23 | 7.5 | 3.6 | 2.2 | Blue |
| Embodiment 24 | 7.4 | 3.8 | 2.3 | Blue |
| Embodiment 25 | 7.5 | 3.4 | 2.1 | Blue |
| Control embodiment 2 | 8.2 | 1.3 | 0.8 | Blue |

According to Table 2 and Table 3, under a same current density (10 mA/cm$^2$), comparing with the photoelectric apparatus described in the control embodiments 1-2, the photoelectric apparatus described in the embodiments 16-25, which have the disclosed compounds as host material or co-doping material, may have lower drive voltages, higher current efficiencies, and higher external quantum efficiencies. That is, the organic photoelectric apparatus having the disclosed compounds may have better performance. Thus, the disclosed compounds may be used as the host materials, and/or the co-doping materials of the organic layers of the photoelectric apparatus.

The above detailed descriptions only illustrate certain exemplary embodiments of the present invention, and are not intended to limit the scope of the present invention. Those skilled in the art can understand the specification as whole and technical features in the various embodiments can be combined into other embodiments understandable to those persons of ordinary skill in the art. Any equivalent or modification thereof, without departing from the spirit and principle of the present invention, falls within the true scope of the present invention.

What is claimed is:

1. A nitrogen-containing heterocyclic compound having a general formula (I):

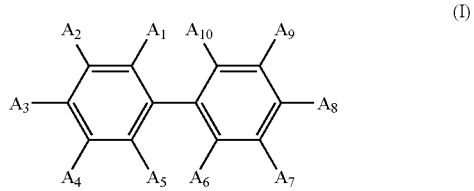

(I)

wherein $A_1$, $A_2$, $A_3$, $A_4$, $A_5$, $A_6$, $A_7$, $A_8$, $A_9$, and $A_{10}$ are independently selected from a nitrile group and a functional group having a general formula (II), and $A_1$, $A_2$, $A_3$, $A_4$, $A_5$, $A_6$, $A_7$, $A_8$, $A_9$, and $A_{10}$ include at least one nitrile group and at least one functional group having the general formula (II), the general formula (II) being:

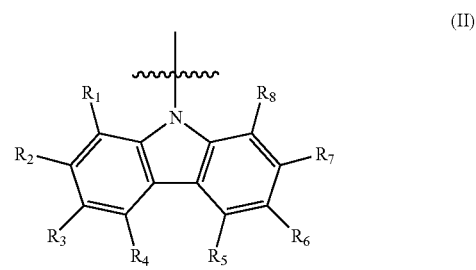

(II)

where $R_1$, $R_2$, $R_3$, $R_4$, $R_5$, $R_6$, $R_7$, and $R_8$ are independently selected from hydrogen atoms, deuterium atoms, $C_{6-30}$ aromatic group and $C_{2-30}$ heterocyclic aromatic group.

2. The nitrogen-containing heterocyclic compound according to claim 1, wherein:

$A_1$, $A_2$, $A_3$, $A_4$, and $A_5$ include at least one nitrile group and at least one functional group having the general formula (II); and $A_6$, $A_7$, $A_8$, $A_9$, and $A_{10}$ include at least one nitrile group and at least one functional group having the general formula (II).

3. The nitrogen-containing heterocyclic compound according to claim 1, wherein:

$A_1$, $A_2$, $A_3$, $A_4$, and $A_5$ include at least one nitrile group without having a functional group having the general formula (II);

$A_6$, $A_7$, $A_8$, $A_9$, and $A_{10}$ include at least one functional group having the general formula (II) without having a nitrile group; and a quantity of the at least one nitrile group in $A_1$, $A_2$, $A_3$, $A_4$, and $A_5$ is less than or equal to a quantity of the functional group having the general formulation (II) in $A_6$, $A_7$, $A_8$, $A_9$, and $A_{10}$.

4. The nitrogen-containing heterocyclic compound according to claim 1, wherein:

an energy level difference ($\Delta E_{st}$) between a lowest singlet state $S_1$ and a lowest triplet state $T_1$ of the nitrogen-containing heterocyclic compound is smaller than or equal to approximately 0.30 eV.

5. The nitrogen-containing heterocyclic compound according to claim 1, wherein:

$R_1$, $R_2$, $R_3$, $R_4$, $R_5$, $R_6$, $R_7$, and $R_8$ are all hydrogen.

6. The nitrogen-containing heterocyclic compound according to claim 1, comprising one of:

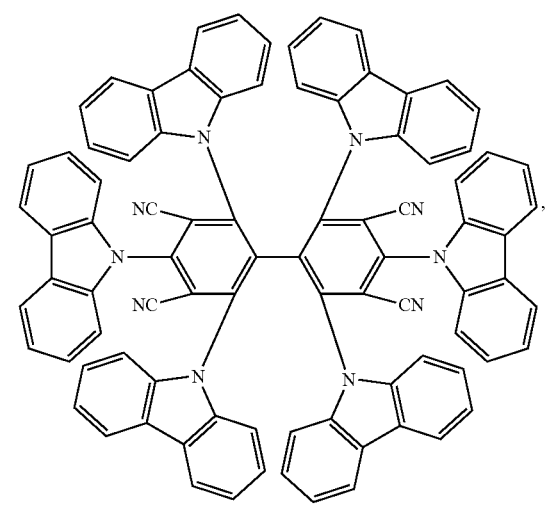

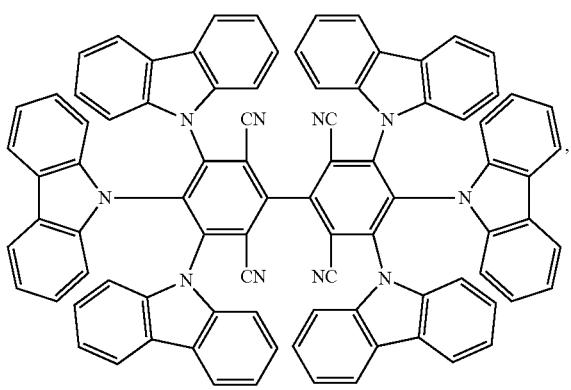

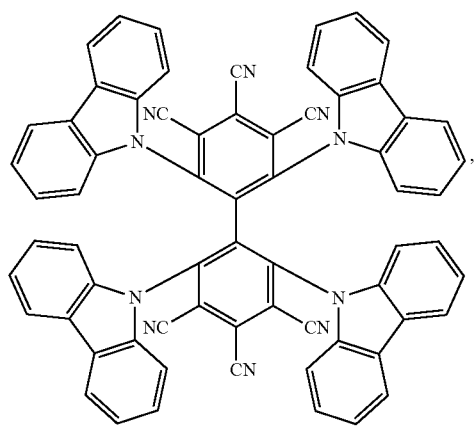

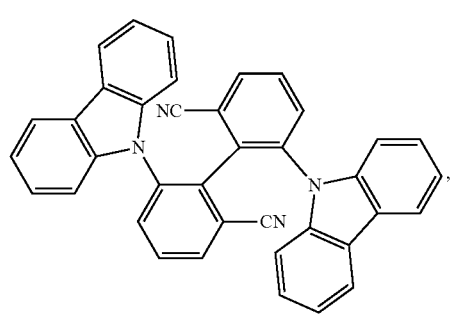

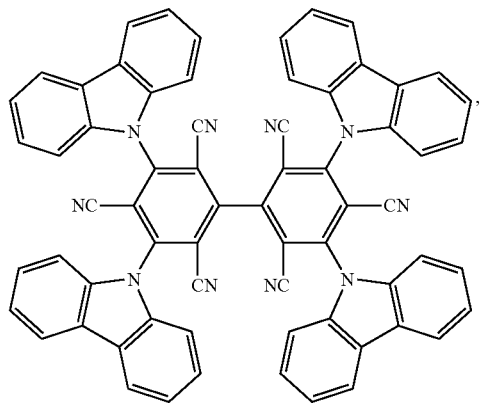

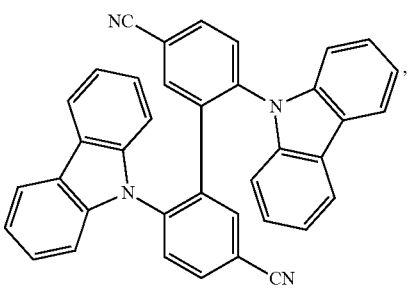

7. The nitrogen-containing heterocyclic compound according to claim 1, comprising:
a thermally activated delayed fluorescence performance.

8. An organic photoelectric apparatus, comprising:
an anode substrate;
at least one organic layer formed over the anode substrate; and
a cathode layer formed over the organic layer,
wherein the at least one organic layer includes at least one nitrogen-containing heterocyclic compound of general formula (I):

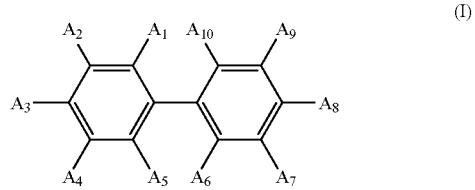

wherein $A_1$, $A_2$, $A_3$, $A_4$, $A_5$, $A_6$, $A_7$, $A_8$, $A_9$, and $A_{10}$ are independently selected from a nitrile group and a functional group having a general formula (II), and $A_1$, $A_2$, $A_3$, $A_4$, $A_5$, $A_6$, $A_7$, $A_8$, $A_9$, and $A_{10}$ include at least one nitrile group and at least one functional group having the general formula (II), the general formula (II) being:

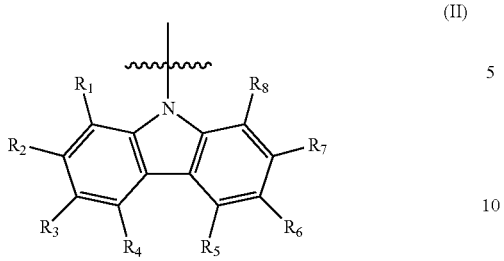

(II)

where $R_1$, $R_2$, $R_3$, $R_4$, $R_5$, $R_6$, $R_7$, and $R_8$ are independently selected from hydrogen atoms, deuterium atoms, $C_{6-30}$ aromatic group and $C_{2-30}$ heterocyclic aromatic group.

9. The organic photoelectric apparatus according to claim 8, wherein the organic layer comprises:
at least one light-emitting layer; and
the at least one light emitting layer includes one or at least two nitrogen-containing heterocyclic compounds.

10. The organic photoelectric apparatus according to claim 9, wherein the organic layer further comprises:
one or at least two of a hole transport layer, a hole injection layer, a hole barrier layer, an electron transport layer, an electron injection layer and an electron barrier layer.

11. The organic photoelectric apparatus according to claim 9, wherein:
the one or at least two nitrogen-containing heterocyclic compounds are used as one of a host material, a doping material and a co-doping material of the at least one light-emitting layer.

12. The organic photoelectric apparatus according to claim 11, wherein:
the one or at least two nitrogen-containing heterocyclic compounds are the host material of the at least one light-emitting layer.

13. The organic photoelectric apparatus according to claim 8, wherein:
an energy level difference ($\Delta E_{st}$) between a lowest singlet state $S_1$ and a lowest triplet state $T_1$ of the nitrogen-containing heterocyclic compound is smaller than or equal to approximately 0.30 eV.

14. A method for fabricating an organic photoelectric apparatus, comprising:
providing an anode substrate,
forming at least one organic layer over the anode substrate; and
forming a cathode layer over the organic layer,
wherein the at least one organic layer includes at least one nitrogen-containing heterocyclic compound having a general formula (I),

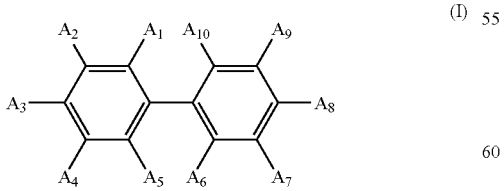

(I)

wherein $A_1$, $A_2$, $A_3$, $A_4$, $A_5$, $A_6$, $A_7$, $A_8$, $A_9$, and $A_{10}$ are independently selected from a nitrile group and a functional group having a general formula (II), and $A_1$, $A_2$, $A_3$, $A_4$, $A_5$, $A_6$, $A_7$, $A_8$, $A_9$, and $A_{10}$ include at least one nitrile group and at least one functional group having the general formula (II), the general formula (II) being:

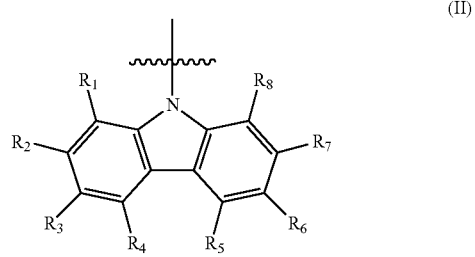

(II)

wherein $R_1$, $R_2$, $R_3$, $R_4$, $R_5$, $R_6$, $R_7$, and $R_8$ are independently selected from hydrogen atoms, deuterium atoms, $C_{6-30}$ aromatic group and $C_{2-30}$ heterocyclic aromatic group.

15. The method according to claim 14, wherein the at least one organic layer comprises:
at least one light-emitting layer; and
the at least one light emitting layer includes one or at least two nitrogen-containing heterocyclic compounds.

16. The method according to claim 14, wherein forming the at least one organic layer further comprises:
forming a hole transport layer on the anode substrate;
forming a light-emitting layer on the hole transport layer;
forming a hole barrier layer on the light-emitting layer;
forming an electron transport layer on the hole barrier layer; and
forming an electron injection layer on the electron transport layer.

17. The method according to claim 15, wherein:
the one or at least two nitrogen-containing heterocyclic compounds are used as one of a host material, a doping material, and a co-doping material of the at least one light-emitting layer.

18. The method according to claim 14, wherein:
the organic layer is formed by an evaporation process.

19. The method according to claim 14, wherein:
an energy level difference ($E_{st}$) among a lowest singlet state $S_1$ and a lowest triplet state $T_1$ of the nitrogen-containing heterocyclic compound is smaller than or equal to approximately 0.30 eV.

20. The method according to claim 14, wherein:
the nitrogen-containing heterocyclic compound comprises a thermally activated delayed fluorescence performance.

* * * * *